United States Patent
Yam et al.

(10) Patent No.: US 12,402,524 B2
(45) Date of Patent: Aug. 26, 2025

(54) DENDRIMERS CONTAINING LUMINESCENT PLATINUM(II) COMPOUNDS FOR ORGANIC LIGHT-EMITTING DEVICES AND THEIR PREPARATION

(71) Applicant: THE UNIVERSITY OF HONG KONG, Hong Kong (CN)

(72) Inventors: Vivian Wing-Wah Yam, Hong Kong (CN); Ka-Wai Kong, Hong Kong (CN); Man-Chung Tang, Hong Kong (CN); Mei-Yee Chan, Hong Kong (CN)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 1010 days.

(21) Appl. No.: 16/606,846

(22) PCT Filed: Apr. 16, 2018

(86) PCT No.: PCT/CN2018/083172
§ 371 (c)(1),
(2) Date: Oct. 21, 2019

(87) PCT Pub. No.: WO2018/192436
PCT Pub. Date: Oct. 25, 2018

(65) Prior Publication Data
US 2020/0052229 A1 Feb. 13, 2020

Related U.S. Application Data

(60) Provisional application No. 62/487,152, filed on Apr. 19, 2017.

(51) Int. Cl.
*H10K 85/30* (2023.01)
*C07F 15/00* (2006.01)
(Continued)

(52) U.S. Cl.
CPC ....... *H10K 85/346* (2023.02); *C07F 15/0086* (2013.01); *C09K 11/06* (2013.01);
(Continued)

(58) Field of Classification Search
CPC .............. C09K 11/06; C09K 2211/185; C09K 2211/1059; C09K 2211/1062;
(Continued)

(56) References Cited

U.S. PATENT DOCUMENTS

| | | | | |
|---|---|---|---|---|
| 2005/0247911 A1* | 11/2005 | Burn | ............ | H01L 51/0085 252/301.35 |
| 2007/0224447 A1* | 9/2007 | Sotoyama | ............ | C09K 11/06 548/402 |
| 2013/0277617 A1* | 10/2013 | Pan | ............ | H10K 85/115 252/500 |

FOREIGN PATENT DOCUMENTS

| | | | |
|---|---|---|---|
| JP | 2008069268 A | * | 3/2008 |
| JP | 2011-129744 A | | 6/2011 |
| WO | WO-2009/086209 A2 | | 7/2009 |

OTHER PUBLICATIONS

English translation of JP 2008069268 A obtained from Global Dossier (Year: 2008).*

(Continued)

*Primary Examiner* — Jennifer A Boyd
*Assistant Examiner* — Braelyn R Watson
(74) *Attorney, Agent, or Firm* — SALIWANCHIK, LLOYD & EISENSCHENK

(57) ABSTRACT

Disclosed is a class of dendrimers containing cyclometalated tridentate platinum(II) compounds with one monoanionic auxiliary ligand, both coordinated to a platinum (II) metal center and having the chemical structure shown in generic formula (I), wherein at least one of $R_1$, $R_2$ and $R_3$ being a dendrimeric moiety of general formula (II), each being optionally substituted.

(Continued)

US 12,402,524 B2
Page 2

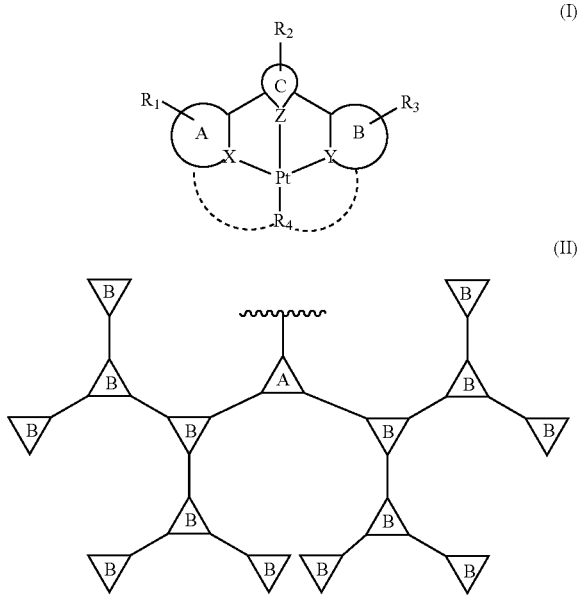

12 Claims, 8 Drawing Sheets

(51) Int. Cl.
  C09K 11/06        (2006.01)
  H10K 50/11        (2023.01)
  H10K 71/12        (2023.01)
  H10K 71/16        (2023.01)
  H10K 101/10       (2023.01)
(52) U.S. Cl.
  CPC .......... C09K 2211/1059 (2013.01); C09K
         2211/1062 (2013.01); C09K 2211/1074
         (2013.01); C09K 2211/185 (2013.01); H10K
         50/11 (2023.02); H10K 71/12 (2023.02); H10K
         71/164 (2023.02); H10K 2101/10 (2023.02)
(58) Field of Classification Search
  CPC ....... C09K 2211/1074; C09K 2211/182; C07F
         15/0006; C07F 15/0086; H01L 51/0087;
         H01L 51/0003; H01L 51/001; H01L
         51/5016; H10K 85/346; H10K 50/11;
         H10K 71/12; H10K 71/164; H10K
         2101/10; C07D 209/86; C07D 209/88;
         C07D 271/107; C07D 403/14; C07D
         413/14
  See application file for complete search history.

(56) References Cited

OTHER PUBLICATIONS

Wang, Zhao, et al. "Neutral and cationic NCN pincer platinum (II) complexes with 1, 3-bis (benzimidazol-2'-yl) benzene ligands: synthesis, structures, and their photophysical properties." Organometallics 33.7 (2014): 1563-1573. (Year: 2014).*
Li, Hui, et al. "Synthesis, characterization and electrophosphorescent properties of mononuclear platinum (II) complexes based on 2-phenylbenzoimidazole derivatives." Journal of Organometallic Chemistry 694.17 (2009): 2777-2785. (Year: 2014).*
Zhao, Tianchu, et al. "Synthesis, tunable photophysics and nonlinear absorption of terpyridyl Pt (II) complexes bearing different acetylide ligands." Dyes and Pigments 126 (2015): 165-172. (Year: 2015).*
Li, Hui, et al. "Design, synthesis, and optoelectronic properties of dendrimeric Pt (II) complexes and their ability to inhibit intermolecular interaction." Inorganic Chemistry 53.2 (2014): 810-821. (Year: 2014).*
Tang, Man-Chung, et al. "Dendritic Luminescent Gold (III) Complexes for Highly Efficient Solution-Processable Organic Light-Emitting Devices." Angewandte Chemie 125.1 (2013): 464-467. (Year: 2013).*
Tang, Huaijun, et al. "Three cationic iridium (III) complexes with 1, 10-phenanthroline or compounds containing 1, 10-phenanthroline unit as auxiliary ligands: Synthesis and application in polymer light-emitting diodes." Dyes and Pigments 131 (2016): 340-348. (Year: 2016).*
Liu, Yu, et al. "Red polymer light-emitting devices based on an oxadiazole-functionalized europium (III) complex." Materials Chemistry and Physics 143.3 (2014): 1265-1270. (Year: 2014).*
Tang, Man-Chung, et al. "Bipolar gold (III) complexes for solution-processable organic light-emitting devices with a small efficiency roll-off." Journal of the American Chemical Society 136.51 (2014): 17861-17868. (Year: 2014).*
Tang, C.W. et al., "Organic electroluminescent diodes", Applied Physics Letters, 51(12): 913-915, Sep. 21, 1987, American Institute of Physics.
Burroughes, J.H. et al., "Light-emitting diodes based on conjugated polymers", Letters to Nature, Oct. 11, 1990, 347:539-541, Nature Publishing Group.
Burrows, P.E. et al., "Prospects and applications for organic light-emitting devices", Current Opinion in Solid State & Materials Science, 1997, pp. 236-243, Current Chemistry Ltd ISSN 1359-0286.
Burn, P.L. et al., "The Development of Light-Emitting Dendrimers for Displays", Advanced Materials, 2007, 19:1675-1688, Wiley-VCH Verlag GmbH & Co. KGaA, Weinheim.
Li, J. et al., "Dendrimers for organic light-emitting diodes", Journal of Materials Chemistry, 2009, 19:7584-7591, The Royal Society of Chemistry.
Wang, P.W. et al., "Electroluminescent Diodes from a Single-Component Emitting Layer of Dendritic Macromolecules", Advanced Materials, 1996, 8(3):237-241, VCH Verlagsgesellschaft mbH, D-69469 Weinheim, 1996.
Halim, M. et al., "Conjugated Dendrimers for Light-Emitting Diodes: Effect of Generation", Advanced Materials, 1999, 11(5):371-374, Wiley-VCH Verlag GmbH, D-69469 Weinheim, 1999.
Ding, J. et al., "Highly Efficient Green-Emitting Phosphorescent Iridium Dendrimers Based on Carbazole Dendrons", Advanced Functional Materials, 2006, 16:575-581, Wiley-VCH Verlag GmbH & Co. KGaA, Weinheim.
Zhou, G. et al., Triphenylamine-Dendronized Pure Red Iridium Phosphors with Superior OLED Efficiency/Color Purity Trade-Offs, Angewandte Chemie Int. Ed., 46:1149-1151, Wiley-VCH Verlag GmbH & Co. KGaA, Weinheim.
Cárdenas, D.J. et al., "Divergent Behavior of Palladium(II) and Platinum(II) in the Metalation of 1,3-Di(2-pyridyl)benzene", Organometallics, 1999, 18:3337-3341, American Chemical Society.
Tam, A.Y.Y. et al., "A luminescent cyclometalated platinum(II) complex and its green organic light emitting device with high device performance", Chem. Communication, 2011, 47:3383-3385, The Royal Society of Chemistry.
Chan, A.K.W. et al., "Synthesis and Characterization of Luminescent Cyclometalated Platinum(II) Complexes of 1,3-Bis-Hetero-Azolylbenzenes with Tunable Color for Applications in Organic Light-Emitting Devices through Extension of π Conjugation by Variation of the Heteroatom", Chem. Eur. J., 2013, 19:13910-13924, Wiley-VCH Verlag GmbH & Co. KGaA, Weinheim.
Lam, E.S.H. et al., "Luminescent Platinum(II) Complexes of 1,3-Bis(N-alkylbenzimidazol-2'yl)benzene-Type Ligands with Potential Applications in Efficient Organic Light-Emitting Diodes", Chem. Eur. J., 2013, 19:6385-6397, Wiley-VCH Verlag GmbH & Co. KGaA, Weinheim.

(56) References Cited

OTHER PUBLICATIONS

Kong, F.K.W. et al., "Design Strategy for High-Performance Dendritic Carbazole-Containing Alkynylplatinum(II) Complexes and Their Application in Solution-Processable Organic Light-Emitting Devices", Journal of the American Chemical Society, 2016, 138:6281-6291, American Chemical Society.

Wong, K.T. et al., "Synthesis and Properties of Dumbbell-Shaped Dendrimers Containing 9-Phenylcarbazole Dendrons", Organic Letters, 2007, 9(22):4531-4534, American Chemical Society.

International Search Report dated Jul. 18, 2018 in International Application No. PCT/CN2018/083172.

Chan, M.H.Y. et al., "Synthesis and Photochromic Studies of Dithienylethene-Containing Cyclometalated Alkynylplatinum(II) 1,3-Bis(N-alkylbenzimidazol-2'-yl)benzene Complexes", Inorganic Chemistry, 2016, 55:5570-5577, American Chemical Society.

Wang, Z. et al., "Neutral and Cationic NCN Pincer Platinum(II) Complexes with 1,3-Bis(benzimidazol-2'-yl)benzene Ligands: Synthesis, Structures, and Their Photophysical Properties", Organometallics, 2014, 33:1563-1573, American Chemical Society.

Chan, A.K.W. et al., "Synthesis and Characterization of Luminescent Cyclometalated Platinum(II) Complexes of 1,3-Bis-Hetero-Azolylbenzenes with Tunable Color for Applications in Organic Light-Emitting Devices through Extension of π Conjugation by Variation of the Heteroatom", Chemistry A European Journal, 2013, 19:13910-13924, Wiley-VCH Verlag GmbH & Co. KGaA, Weinheim.

Lam, E.S.H. et al., "Luminescent Platinum(II) Complexes of 1,3-Bis(N-alkylbenzimidazol-2'-yl)benzene-Type Ligands with Potential Applications in Efficient Organic Light-Emitting Diodes", Chemistry A European Journal, 2013, 19:6385-6397, Wiley-VCH Verlag GmbH & Co. KGaA, Weinheim.

\* cited by examiner

DENDRIMERS CONTAINING LUMINESCENT PLATINUM(II) COMPOUNDS FOR ORGANIC LIGHT-EMITTING DEVICES AND THEIR PREPARATION

CROSS-REFERENCE TO RELATED APPLICATIONS

This application is the U.S. national stage application of International Patent Application No. PCT/CN2018/083172, filed Apr. 16, 2018, which claims the benefit of U.S. Provisional Application No. 62/487,152, filed Apr. 19, 2017, the disclosure of each of which is incorporated herein by reference in its entirety.

FIELD OF THE INVENTION

Embodiments of the invention are directed to a novel class of dendrimers containing cyclometalated tridentate platinum(II) compounds and the syntheses of these compounds. These solution-processable or evaporable compounds can be used as light-emitting material in phosphorescence organic light-emitting devices (OLEDs).

BACKGROUND OF THE INVENTION

With the advantages of low cost, light weight, low operating voltage, high brightness, robustness, color tunability, wide viewing angle, ease of fabrication onto flexible substrates as well as low energy consumption, OLEDs are considered as remarkably attractive candidates for flat panel display technologies and for solid-state lightings. Transition metal complexes are an important class of materials in making OLEDs due to the presence of the heavy metal center, which can effectively lead to a strong spin-orbit coupling and thus promotes an efficient intersystem crossing to give phosphorescence. This can result in theoretically a four-fold enhancement in the internal quantum efficiency of the OLEDs to reach 100% due to the harvesting of both triplet and singlet excitons.

Typically an OLED consists of several layers of semiconductor sandwiched between two electrodes. The cathode is composed of a low work function metal or metal alloy deposited by vacuum evaporation, whereas the anode is a transparent conductor such as indium-tin oxide (ITO). Upon the application of a DC voltage, holes injected by the ITO electrode and electrons injected by the metal electrode will recombine to form excitons. Subsequent relaxation of excitons will then result in the generation of electroluminescence (EL).

The breakthroughs that led to the exponential growth of this field and to its first commercialized products can be traced to two pioneering demonstrations. In 1987, Tang and VanSlyke [Tang, C. W.; VanSlyke, S. A. Appl. Phys. Lett. 51, 913 (1987)] proposed the use of a double-layer structure of vacuum deposited, small-molecular films, in which tris(8-hydroxyquinoline)aluminum($Alq_3$) was utilized both as light-emitting layer and electron-transporting layer. Later, the first polymeric light-emitting device was pioneered by Burroughs et al. in 1990 [Burroughs, J. H.; Bradley, D. D. C.; Brown, A. R.; Marks, N.; Friend, R. H.; Burn, P. L.; Holmes, A. B. Nature 347, 539 (1990)], in which a yellow-green EL from poly(p-phenylenevinylene) (PPV) was realized. Since then, a number of new electroluminescent small molecular based and polymeric light-emitting materials have been investigated with improved light-emitting properties. The key advantage of using polymers as light-emitting materials is that they are highly soluble in most organic solvents, and the devices can be easily fabricated by using low-cost and efficient wet processing techniques, such as spin-coating, screen-printing, or ink jet printing [Burrows, P. E.; Forrest, S. R.; Thompson, M. E. Curr. Opin. Solid State Mat. Sci. 2, 236 (1997)].

Apart from the development of small molecular and polymeric materials, recent demonstrations on the design and synthesis of dendrimers as light-emitting materials provide another new and interesting direction. Dendrimers are macromolecules with well-defined size and number of peripheral groups. These materials are typically comprised of three parts: a core unit, surrounding dendrons, and peripheral groups. The branching levels of the surrounding dendrons determine the dendrimer generation, in which the peripheral groups attached onto the surface of the surrounding dendrons can control the intermolecular interactions, solubility, viscosity and processability of the dendrimers. The emissive chromophores of the dendrimers can be located at the core of the dendrimer, within the surrounding dendrons or at the peripheral groups of the dendrimers. Typically, emissive chromophores are usually attached at the core units. In general, dendrimers can be divided into two classes, conjugated dendrons and saturated dendrons. The branching point of the conjugated dendrons or dendrimers has to be fully conjugated but not essentially delocalized [Burn, P. L.; Lo, S. C.; Samuel, I. D. W. Adv. Mater. 19, 1675 (2007)].

The distinct properties of dendrimers allow them to be good candidates in making OLEDs. Unlike polymers, dendrimers show a well-defined structure and precise molecular weight, in which the purity of the products can be well controlled and are reproducible; both of which are crucial factors for commercialization. In addition, their high solubility in most organic solvents opens up a possibility to fabricate the devices by solution-processed techniques such as spin-coating and ink jet printing. Such techniques not only are essential for the patterning of large-area displays and solid-state lighting panels, but also avoid the use of the expensive and high-temperature vacuum evaporation technique that is needed for preparing small molecular based OLEDs. More importantly, the dendrimer generation can control the intermolecular interactions. Intermolecular interactions are well-known to have an influence on the efficiency of OLEDs. Indeed, many emitters show strong luminescent properties in solution. However, the strong intermolecular interactions present in the solidstate lead to the formation of dimer, excimer or aggregate so as to lower the efficiency of the OLEDs. At high current density, the triplet-triplet annihilation tends to further lower the performance. In view of these, the introduction of bulky peripheral groups can keep the molecules apart to avoid these problems. Furthermore, the color of light emission can be fine-tuned by simply choosing different combinations of the cores, dendrimer generations and type of peripheral groups. For instance, compounds with the same branching level of surrounding dendrons and surface groups incorporated to different cores can lead to different color emission. The glass transition temperature of these macromolecules is usually high, giving a good operation stability of the devices [Liu, D.; Li, J. Y. J. Mater. Chem. 19, 7584 (2009)].

The first OLED with dendrimers as light-emitting materials was first demonstrated by Wang et al. [Wang, P. W.; Liu, Y. J.; Devadoss, C.; Bharathi, P.; Moore, J. S. Adv. Mater. 8, 237 (1996)]. These dendrimers contain a highly fluorescent core, 9,10-bis(phenylethynyl) anthracene, a phenylacetylene as surrounding dendron for electron capture, and tertiary butyl group as the peripheral group to maintain its solubility. Such devices exhibited two major photoluminescence bands at 480 and 510 nm and a broad, structureless emission band at 600 nm; however, the device performance was rather low and indeed no efficiency data was reported. Later on, Halim et al. reported a family of conjugated light-emitting dendrimers based on the PPV structure [Halim, M.; Pillow, N. G.; Samuel, I. D. W.; Burn, P. L. *Adv. Mater.* 11, 371 (1999)]. These dendrimers consist of a distyrylbenzene core for blue color emission, stilbene dendrons, and tert-butyl groups as peripheral groups for solution processing properties. All three generations of dendrimers could be spin-coated to form amorphous thin films from chloroform and showed a blue emission in the photoluminescence spectrum. A red shift was observed in the EL spectrum for the first generation dendrimer. With increasing the bulky groups to form different generation dendrimers, concentration quenching effects were substantially suppressed. This demonstrated that dendrimers can effectively inhibit the intermolecular interactions and the formation of dimer, excimer or aggregate.

While solution-processable OLEDs based on fluorescent dendrimers have been realized, their efficiencies are usually quite low, and can be as low as 0.1%. In order to improve the device performance, it is desirable to make use of spin-orbit coupling in order to mix both singlet and triplet excited states. Hence, the use of heavy metal complexes in OLEDs is preferred over purely organic materials. Recently, a series of green-emitting carbazole conjugated dendrimers containing iridium(III) complexes have been reported by Ding et al. [Ding, J. Q.; Gao, J.; Cheng, Y.; Xie, Z; Wang, L. X.; Ma, D.; Jing, X. B.; Wang, F. S. *Adv. Funct. Mater.* 16, 571 (2006)]. By taking the advantages of the dendritic structure, high solubility, non-doped, low cost and solution-processable OLEDs had been achieved. With the increasing generation of the dendrons, the intermolecular interactions can be significantly reduced, and good hole-transporting properties of carbazoles can be obtained. Superior device performance had been obtained, in which a peak external quantum efficiency (EQE) of 10.3% and current efficiency (CE) of 34.7 cd A$^{-1}$ were achieved for a non-doped green-emitting OLED. Meanwhile, red-emitting triphenylamine dendrimers containing iridium(III) complexes had also been reported in 2007 [Zhou, G. J.; Wang, W. Y.; Yao, B.; Xie, Z. Y.; Wang, L. X. *Angew. Chem. Int. Ed.* 46, 1149 (2007)]. The extended π-conjugated system of triphenylamine dendrons raises the highest occupied molecular orbital (HOMO) level, and the electron-rich triphenylamine moieties facilitate an efficient hole injection from the anode. High EQE and CE of the devices of 7.4% and 3.7 cd A$^{-1}$, respectively, were reached, even higher or comparable to the vacuum deposited devices with similar Commission Internationale de L'Eclariage (CIE) color. This indicates that dendrimers are one of the promising light-emitting materials for solution-processable OLEDs.

Apart from the OLEDs based on iridium(III) complexes, platinum(II) complexes are another class of promising phosphorescent emitters because of their high luminescence quantum yields, short excited-state lifetimes, as well as high thermal and electrochemical stabilities. Specifically, tridentate 1,3-dipyridylbenzene (N^C^N) cyclometalated platinum (II) complexes represent one of the important candidates for phosphorescent OLED(PHOLED) application due to their versatility in molecular design and ease of synthesis [Cárdenas, D. J.; Arellano, A. M. E. *Organometallics* 1999, 18, 3337]. In 2011, Yam and coworkers reported highly luminescent tridentate cyclometalated platinum(II) complexes based on the 2,6-bis(N-alkyl-benzimidazol-2'-yl)benzene (bzimb) as the pincer ligand for the preparation of OLEDs by vapor deposition [Tam, A. Y.-Y.; Tsang, D. P.-K.; Chan, M.-Y.; Zhu, N.; Yam, V. W.-W. *Chem. Commun.* 47, 3383 (2011)]. The optimized OLED reached an EQE of 11.5% and a CE of 38.9 cd A$^{-1}$. Later on, Yam and co-workers further reported a related series of cyclometalated platinum (II) complexes with the N^C^N ligands of 2,6-bis(benzoxazol-2'-yl)benzene (bzoxb), 2,6-bis(benzothiazol-2'-yl)benzene (bzthb), and 2,6-bis(N-alkylnaphthoimidazol-2'-yl) benzene (naphimb) to fine-tune the emission colors ranging from yellow to red [Chan, A. K.-W.; Lam, E. S.-H.; Tam, A. Y.-Y.; Tsang, D. P.-K.; Lam, W. H.; Chan, M.-Y.; Wong, W.-T.; Yam, V. W.-W. *Chem. Eur. J.* 2013, 19, 13910]. Selected platinum(II) complexes had also been utilized as phosphorescent dopants for PHOLEDs, in which a saturated yellow emission with CIE coordinates of (0.50, 0.49), maximum CE of 16.9 cd A$^{-1}$ and EQE of 6.9% have been achieved. This suggested that the platinum(II) complexes are promising phosphorescent materials in terms of efficiency and thermal stability. Yet, the library of solution-processable platinum(II) complexes is rather small, and their EL performances are generally inferior to those of vacuum-deposited counterparts. For example, solution-processable PHOLEDs based on [Pt(bzimb)(C≡C—C$_6$H$_4$-carbazole)] had been reported and the EQEs were rather low (i. E. 3.4%) [Lam, E. S.-H.; Tam, A. Y.-Y.; Tsang, D. P.-K.; Lam, W. H.; Chan, M.-Y.; Yam, V. W.-W. *Chem. Eur. J.* 2013, 19, 6385]. The poor performance is possibly attributed to the limited solubility in the organic solvent. In order to tackle this difficulty, Yam and coworkers first reported a new class of solution-processable platinum(II) complexes with the incorporation of the carbazole dendrimer as the auxiliary ligand to improve the limited solubility [Kong, F. K.-W.; Tang, M.-C.; Wong, Y.-C.; Chan, M.-Y.; Yam, V. W.-W. *J. Am. Chem. Soc.*, 2016, 138, 6281]. More importantly, high performance solution-processable PHOLEDs with a remarkable maximum CE and EQE of 37.6 cd A$^{-1}$ and 10.4% have been realized, respectively. To the best of our knowledge, the integration of dendrimer-containing cyclometalating tridentate ligands to the platinum(II) centers with a substituted or non-substituted monoanionic ligand that is optionally linked or unlinked to the tridentate ligand has not yet been reported in the literature. More importantly, this novel class of emitting materials can be fabricated by using low cost, low material-consuming, and high efficiency solution-processing, vacuum deposition or other fabrication techniques to prepare high performance phosphorescence-based OLEDs.

The present invention discloses herein in the design, synthesis and photoluminescence behavior of luminescent platinum(II) dendrimers, and their device fabrication using solution-processing, vacuum deposition or other fabrication techniques to produce high efficiency PHOLEDs.

BRIEF SUMMARY OF THE INVENTION

Embodiments of the invention are directed to novel luminescent cyclometalated platinum(II) dendrimers and their preparation. Other embodiments of the invention are directed to OLEDs from the novel luminescent platinum(II) dendrimers.

The novel luminescent platinum(II) dendrimers are conjugated dendrimers attached to tridentate cyclometalating ligands coordinated to a platinum(II) metal center.

The novel luminescent platinum(II) dendrimers have the chemical structure shown in generic formula (I),

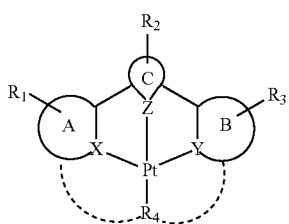

(I)

wherein
a) X, Y and Z are cyclic structures;
b) any combinations of the rings X, Y and Z can be fused together with each other or the rings X, Y and Z can be non-fused with each other;
c) $R_1$, $R_2$ and $R_3$ are the same or different and independently selected from hydrogen, alkyl, alkenyl, alkynyl, alkylaryl, cycloalkyl, OR, $NR_2$, SR, C(O)R, C(O)OR, C(O)$NR_2$, CN, $CF_3$, $NO_2$, $SO_2$, SOR, $SO_3$R, halo, aryl, heteroaryl, heterocyclic group or a dendrimeric moiety of general formula (II), wherein R is independently alkyl, alkenyl, alkynyl, alkyaryl, aryl or cycloalkyl, with at least one of $R_1$, $R_2$, and $R_3$ being a dendrimeric moiety of general formula (II), each being optionally substituted;

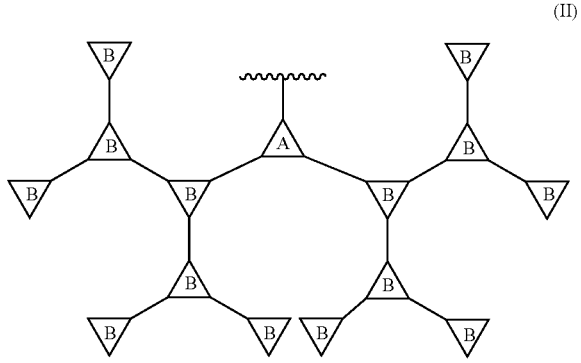

(II)

wherein:
(i) Unit A is the central part of the dendron and the branching point of the dendrimer;
(ii) Unit B is the surface groups or dendron of the dendrimer, or none;
d) $R_4$ is an optionally substituted ligand attached to the platinum(II) atom that is optionally linked or unlinked to the tridentate ligand.

In accordance with the present invention, these novel luminescent platinum(II) dendrimers show strong photoluminescence via triplet excited state upon photo-excitation, or EL via triplet exciton upon applying a DC voltage. These compounds according to embodiments of the invention are highly soluble in common organic solvents such as dichloromethane, chloroform and toluene. Alternatively, the compounds can be doped into a host matrix for thin film deposition by spin-coating or ink jet printing or other known fabrication methods. In some embodiments, the compounds can be used for the fabrication of OLEDs as phosphorescent emitters or dopants to generate EL.

As shown in FIG. 1, according to an embodiment of the present invention, the cyclometalated platinum(II) dendrimers are included in a light-emitting layer of OLED. OLED comprises a layered structure having a cathode layer, an electron-transporting layer, luminescent platinum(II) compound as the light-emitting layer, a hole-transporting layer and an anode deposited on glass substrate.

BRIEF DESCRIPTION OF THE DRAWINGS

Scheme 1 is the chemical structures of compounds 1-14.

DETAILED DESCRIPTION OF THE INVENTION

Figure 1:
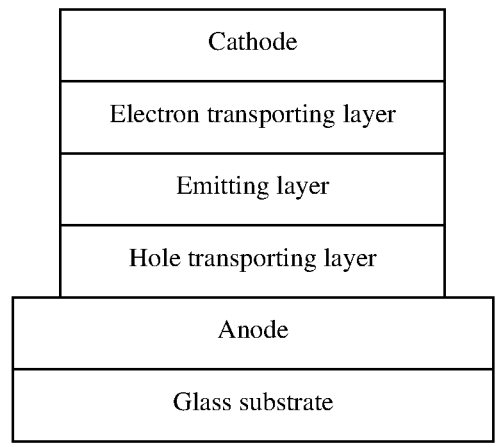
FIG. 1 is a schematic diagram of the basic structure of an OLED, in accordance with an embodiment of the invention.

The present invention is directed to the synthesis and luminescence studies of a novel class of dendrimers containing cyclometalated tridentate platinum(II) compounds with one monoanionic auxiliary ligand, both coordinated to a platinum(II) metal center and having the chemical structure shown in generic formula (I),

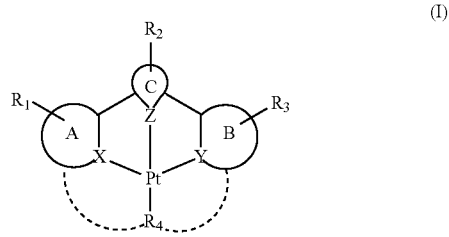

(I)

wherein
a) X, Y and Z are cyclic structures;
b) any combinations of the rings X, Y and Z can be fused together with each other or the rings X, Y and Z can be non-fused with each other;
c) $R_1$, $R_2$ and $R_3$ are the same or different and independently selected from hydrogen, alkyl, alkenyl, alkynyl, alkylaryl, cycloalkyl, OR, $NR_2$, SR, C(O)R, C(O)OR, C(O)$NR_2$, CN, $CF_3$, $NO_2$, $SO_2$, SOR, $SO_3R$, halo, aryl, heteroaryl, heterocyclic group or a dendrimeric moiety of general formula (II), wherein R is independently alkyl, alkenyl, alkynyl, alkyaryl, aryl or cycloalkyl, with at least one of $R_1$, $R_2$, and $R_3$ being a dendrimeric moiety of general formula (II), each being optionally substituted;

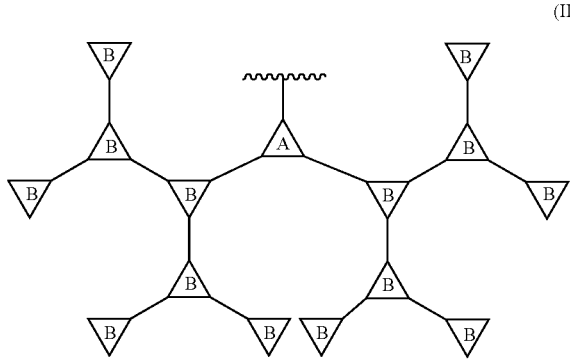

(II)

wherein:
(i) Unit A is the central part of the dendron and the branching point of the dendrimer;
(ii) Unit B is the surface groups or dendron of the dendrimers, or none;
d) $R_4$ is an optionally substituted ligand attached to the platinum(II) atom that is optionally linked or unlinked to the tridentate ligand.

X and Y are independently selected from, but is not limited to, pyridine, imidazole, benzimidazole, naphthoimidazole, quinoline, isoquinoline, quinoxaline, pyrimidine, pyrazine, pyrazole, triazole, tetrazole, pyridazine, triazine, tetrazine, triazole, indole, oxazole, isoxazole, isothiazole, benzothiazole and benzoxazole, each being optionally substituted;

Z is selected from, but is not limited to, benzene, naphthalene, anthracene, pyrene, fluorene, pyrene, pyridine, imidazole, benzimidazole, naphthoimidazole, quinoline, isoquinoline, quinoxaline, pyrimidine, pyrazine, pyrazole, triazole, tetrazole, pyridazine, triazine, tetrazine, triazole, indole, oxazole, isoxazole, isothiazole, benzothiazole, benzoxazole, thiophene, furan, benzofuran and dibenzofuran, each being optionally substituted;

A and B are optionally substituted N or C atom, benzene, phenyl derivatives, pyridine or pyridyl derivatives, thiophene, furan, pyrazole, imidazole, oxazole, isoxazole, thiazole, isothiazole, pyrrole, pyrazine, pyridazine, pyrimidine, benzimidazole, benzofuran, benzothiazole, indole, naphthalene, triazole, tetrazole, pyran, thiapyran, oxadiazole, triazine, tetrazine, carbazole, dibenzothiophene, dibenzofuran, with one or more alkyl, alkenyl, alkynyl, alkylaryl, cycloalkyl, OR, $NR_2$, SR, C(O)R, C(O)OR, C(O)$NR_2$, CN, $CF_3$, $NO_2$, $SO_2$, SOR, $SO_3R$, halo, aryl, heteroaryl, heterocyclic group, wherein R is independently alkyl, alkenyl, alkynyl, alkyaryl, aryl or cycloalkyl, or other appropriate aromatic moieties, each being optionally substituted.

$R_4$ is selected from, but is not limited to, halogen, alkyl, cycloalkyl, alkenyl, arylalkenyl, aryl, alkynyl and arylalkynyl, heteroaryl, heterocyclic group, each being optionally substituted such as by a dendrimeric moiety of general formula (II). In one embodiment, $R_4$ is optionally a substituted monoanionic ligand.

In the present disclosure the following terms are used.

The term "optional" or "optionally" means that the subsequently described event or circumstance may or may not occur, and that the description includes instances where said event or circumstance occurs and instances in which it does not. For example, "optionally substituted alkyl" includes "alkyl" and "substituted alkyl," as defined below. The term "halo" or "halogen" as used herein includes fluorine, chlorine, bromine and iodine. The term "alkyl" as used herein includes straight and branched chain alkyl groups, as well as cycloalkyl group with cyclic structure of alkyl groups. Preferred alkyl groups are those containing from one to eighteen carbon atoms and includes methyl, ethyl, propyl, isopropyl, butyl, isobutyl, tert-butyl, and the like. In addition, the alkyl group may be optionally substituted with one or more substituents selected from OR, $NR_2$, SR, C(O)R, C(O)OR, C(O)$NR_2$, CN, $CF_3$, $NO_2$, $SO_2$, SOR, $SO_3R$, halo and cyclic-amino. The term "alkenyl" as used herein includes both straight and branched chain alkene radicals. Preferred alkenyl groups are those containing two to eighteen carbon atoms. In addition, the alkenyl group may be optionally substituted with one or more substituents selected from OR, $NR_2$, SR, C(O)R, C(O)OR, C(O)$NR_2$, CN, $CF_3$, $NO_2$, $SO_2$, SOR, $SO_3R$, halo and cyclic-amino. The term "alkynyl" as used herein includes both straight and branched chain alkyne radicals. Preferred alkynyl groups are those containing two to eighteen carbon atoms. In addition, the alkynyl group may be optionally substituted with one or more substituents selected from OR, $NR_2$, SR, C(O)R, C(O)OR, C(O)$NR_2$, CN, $CF_3$, $NO_2$, $SO_2$, SOR, $SO_3R$, halo and cyclic-amino. The term "arylalkynyl" as used herein includes an alkynyl group which has an aromatic group as a substituent. In addition, the arylalkynyl group may be optionally substituted with one or more substituents selected from OR, $NR_2$, SR, C(O)R, C(O)OR, C(O)$NR_2$, CN, $CF_3$, $NO_2$, $SO_2$, SOR, $SO_3R$, halo and cyclic-amino. The term "alkylaryl" as used herein includes an alkyl group which has an aromatic group as a substituent. In addition, the alkylaryl group may be optionally substituted with one or more substituents selected from OR, $NR_2$, SR, C(O)R, C(O)OR, C(O)$NR_2$, CN, $CF_3$, $NO_2$, $SO_2$, SOR, $SO_3R$, halo and cyclic-amino; and R is selected from, but is not limited to, aryl, substituted aryl, heteroaryl, substituted heteroaryl, heterocyclic aryl and substituted heterocyclic aryl.

Aryl alone or in combination includes carbocyclic aromatic systems. The systems may contain one, two or three rings wherein each ring may be attached together in a pendant manner or may be fused. Preferably the rings are 5- or 6-membered rings.

Heteroaryl alone or in combination includes heterocyclic aromatic systems. The systems may contain one, two or three rings wherein each ring may be attached together in a pendant manner or may be fused. Preferably the rings are 5- or 6-membered rings.

Heterocyclic and heterocycle refer to a 3 to 7-membered ring containing at least one heteroatom. This includes aromatic rings including but not limited to pyridine, thiophene, furan, pyrazole, imidazole, oxazole, isoxazole, thiazole, isothiazole, pyrrole, pyrazine, pyridazine, pyrimidine, benzimidazole, benzofuran, benzothiazole, indole, naphthalene, triazole, tetrazole, pyran, thiapyran, oxadiazole, triazine, tetrazine, carbazole, dibenzothiophene, dibenzofuran, fluorine, and non-aromatic rings including but not limited to piperazine, piperidine, and pyrrolidine. The groups of the present invention can be substituted or unsubstituted. Preferred substituents include but are not limited to alkyl, alkoxy, aryl.

Heteroatom refers to S, O, N, P, Se, Si, Te.

Substituted refers to any level of substitution although mono-, di- and tri-substitutions are preferred. Preferred substituents include hydrogen, halogen, aryl, alkyl and heteroaryl.

Benzene includes substituted or unsubstituted benzene.

Pyridine includes substituted or unsubstituted pyridine.

Thiophene includes substituted or unsubstituted thiophene.

Furan includes substituted or unsubstituted furan.

Pyrazole includes substituted or unsubstituted pyrazole.

Imidazole includes substituted or unsubstituted imidazole.

Oxazole includes substituted or unsubstituted oxazole.

Isoxazole includes substituted or unsubstituted isoxazole.

Thiazole includes substituted or unsubstituted thiazole.

Isothiazole includes substituted or unsubstituted isothiazole.

Pyrrole includes substituted or unsubstituted pyrrole.

Pyrazine includes substituted or unsubstituted pyrazine.

Pyridazine includes substituted or unsubstituted pyridazine.

Pyrimidine includes substituted or unsubstituted pyrimidine.

Benzimidazole includes substituted or unsubstituted benzimidazole.

Benzofuran includes substituted or unsubstituted benzofuran.

Benzothiazole includes substituted or unsubstituted benzothiazole.

Indole includes substituted or unsubstituted indole.

Naphthalene includes substituted or unsubstituted naphthalene.

Triazole includes substituted or unsubstituted triazole.

Tetrazole includes substituted or unsubstituted tetrazole.

Pyran includes substituted or unsubstituted pyran.

Thiapyran includes substituted or unsubstituted thiapyran.

Oxadiazole includes substituted or unsubstituted oxadiazole.

Triazine includes substituted or unsubstituted triazine.

Tetrazine includes substituted or unsubstituted tetrazine.

Carbazole includes substituted or unsubstituted carbazole.

Dibenzothiophene includes substituted or unsubstituted dibenzothiophene.

Dibenzofuran includes substituted or unsubstituted dibenzofuran.

Piperazine includes substituted or unsubstituted piperazine.

Piperidine includes substituted or unsubstituted piperidine.

Pyrrolidine includes substituted or unsubstituted pyrrolidine.

In some embodiments of the invention, the luminescent platinum(II) compounds are prepared in high purity. The synthetic method involves reacting a tridentate ligand-containing platinum(II) chloride with the corresponding auxiliary ligands under copper-catalyzed reaction condition. This reaction is carried out under a mild condition. Purification can be carried out by any method or combination of methods, including chromatography, extraction, crystallization, sublimation or any combination thereof.

The luminescent platinum(II) complexes can be used to form thin films by vacuum deposition, spin-coating, ink jet printing, or other known fabrication methods that can be applied in OLEDs. Referring to FIG. 1, an OLED has, in order, substrate, hole-injecting anode, hole-transporting layer, light-emitting layer, electron-transporting layer, and electron-injecting cathode.

Substrate is electrically insulated and can be either optically transparent, and comprises glass, plastic foil, or other appropriate material, or alternatively, may be opaque and comprises one or more semiconducting materials or ceramics. In one embodiment of the invention, the EL emission is viewed through substrate, or through both sides of the device, and substrate comprises a transparent glass substrate or a plastic foil. In other embodiments, the EL emission is viewed only through the top electrode, and substrate comprises an opaque semiconductor or ceramic wafers. Hole-injecting anode injects holes into the organic EL layer when anode is positively biased. Anode is composed of a conductive and optionally transmissive layer. In one embodiment of the invention, viewing the EL emission through the substrate is desirable, and hole-injecting anode is transparent. In other embodiments, the EL emission is viewed through the top electrode and the transmissive characteristics of anode are immaterial, and therefore any appropriate materials including metals or metal compounds having a work function of greater than 4.1 eV are used. Appropriate metals include gold, iridium, molybdenum, palladium, and platinum. In some embodiments, anode is transmissive, and suitable materials are metal oxides, including indium-tin oxide, aluminum- or indium-doped zinc oxide, tin oxide, magnesium-indium oxide, nickel-tungsten oxide, and cadmium-tin oxide. The preferred metals and metal oxides can be deposited by evaporation, sputtering, laser ablation, and chemical vapor deposition. Suitable materials for hole-transporting layer include polycyclic aromatic compounds, for example, 4,4'-bis[N-(1-naphthyl)-N-phenylamino]biphenyl (NPB), 4,4'-bis[N-(3-methylphenyl)-N-phenylamino]biphenyl (TPD), 4,4',4"-tris[(3-methylphenyl)phenyl amino] triphenylamine (MTDATA), and di[4-(N,N-ditolyl-amino)phenyl]cyclohexane (TAPC). In addition, polymeric hole-transporting materials can be used including poly(N-vinylcarbazole) (PVK), polythiophene, polypyrrole, polyaniline, and copolymers including poly(3,4-ethylenedioxythiophene):poly(-styrene-surlfonate) (PEDOT:PSS).

Light-emitting layer in FIG. 1 is formed by doping the phosphorescent platinum(II) compound as a dopant into a host compound. Suitable host materials should be selected so that the triplet exciton can be transferred efficiently from the host material to the phosphorescent dopant material. Suitable host materials include certain aryl amines, triazoles and carbazole compounds. Examples of desirable hosts are 4,4'-bis(carbazol-9-yl)biphenyl (CBP), MCP, TCTA, SPPO13, 3-(4-biphenylyl)-4-phenyl-5-tert-butylphenyl-1,2, butylphenyl-1,2,4-triazole (TAZ), p-bis(triphenylsilyl)benzene (UGH2), and PVK.

Electron-transporting layer consists of materials or mixtures of materials having a high ionization potential and wide optical band gap. Suitable electron-transporting materials include 1,3,5-tris(phenyl-2-benzimidazolyl)-benzene (TPBI), bathocuproine (BCP), bathophenanthroline (BPhen) and bis(2-methyl-8-quinolinolate)-4-(phenylphenolate)aluminum (BAlq), tris[2,4,6-trimethyl-3-(pyridin-3-yl)phenyl] borane (3TPyMB), 1,3,5-tri[(3-pyridyl)-phen-3-yl]benzene (TmPyPB), and 1,3-bis[3,5-di(pyridin-3-yl)-phenyl]benzene (BmPyPhB). In one embodiment of the invention, electron-transporting layer is prepared as an organic film by thermal evaporation, spin-coating, ink jet printing from a solution, or other known fabrication methods. Electron-injecting cathode acts as a transmissive electron injector that injects electrons into the organic EL layer of anode when cathode is negatively biased. Cathode comprises a thin fluoride layer (which may be omitted) and a metal or metal alloy, preferably having a work function of less than 4 eV. Suitable materials include Mg:Ag, Ca, Li:Al, Al.

In some embodiments of the invention, novel luminescent platinum(II) complexes are either the primary luminescent material or a secondary luminescent material in device. In some embodiment, the platinum(II) compound is employed as electrophosphorescent dopants in the multilayer solution-processable OLED with an EQE of 16.0%. Advantageously, the platinum(II) compounds can be deposited in the OLEDs by vacuum deposition, spin-coating, screen printing or ink jet printing. The excellent solubilities of these luminescent platinum(II) complexes in a variety of organic solvents permits simple and economic manufacturing and patterning of large-area displays.

In general, emissive layer is sandwiched between hole-transporting layer and electron-transporting layer. To ensure an efficient exothermic energy transfer between the host material and the dopant material, the triplet energy of the host material must be larger than that of the dopant material. In addition, both the ionization potential and the electron affinity of the host material should be larger than those of the dopant material in order to achieve efficient Förster energy transfer from the host to the dopant. In order to confine triplet excitons within emissive layer, the triplet energy of hole-transporting material and electron-transporting material should be larger than that of the dopant material.

The present invention will be illustrated more specifically by the following non-limiting examples, it being understood that changes and variations can be made therein without deviating from the scope and the spirit of the invention as hereinafter claimed. It is also understood that various theories as to why the invention works are not intended to be limiting.

Example 1

Synthesis and Characterization of Dendritic Tridentate Ligands L1-L7

Dendritic tridentate ligands, (Cbz$^t$Bu$_2$-Ph)$_2$bzimb, {(Cbz$^t$Bu$_2$)$_2$-Cbz-Ph}$_2$bzimb, Cbz$^t$Bu$_2$-(Ph$_2$bzimb) and (Cbz$^t$Bu$_2$)$_2$-Cbz-(Ph$_2$bzimb), were synthesized according to the modification of a procedure reported in the literature [Wing, K.-T.; Lin, Y.-H.; Wu, H.-H; Fungo, F. *Org. Lett.* 9, 4531 (2007)]. For example, to a well-degassed solution of 1,3-bis(N-(4-bromophenyl)-benzimidazol-2'-yl)benzene (1.08 g, 1.75 mmol), 3,6-di-tert-butylcarbazole (0.97 g, 3.66 mmol), sodium tert-butoxide (350 mg, 3.66 mmol) and tris(dibenzylideneacetone)dipalladium(0) (80 mg, 0.09 mmol) in toluene (10 mL) was added tri-tert-butylphosphine (18 mg, 0.09 mmol). The resulting mixture was stirred and heated to reflux at 120° C. for 24 h. To the mixture was then added deionized water (20 mL). The organic phase was separated and was washed with brine solution for three times, and then extracted three times with dichloromethane. The organic extract was dried over anhydrous Na$_2$SO$_4$ and filtered. Further purification was done by column chromatography (70-230 mesh) using hexane-ethyl acetate (6:1, v/v) as eluent. Subsequent recrystallization by diffusion of diethyl ether vapor into a concentrated solution of the product gave (Cbz$^t$Bu$_2$-Ph)$_2$bzimb as a white solid (950 mg).

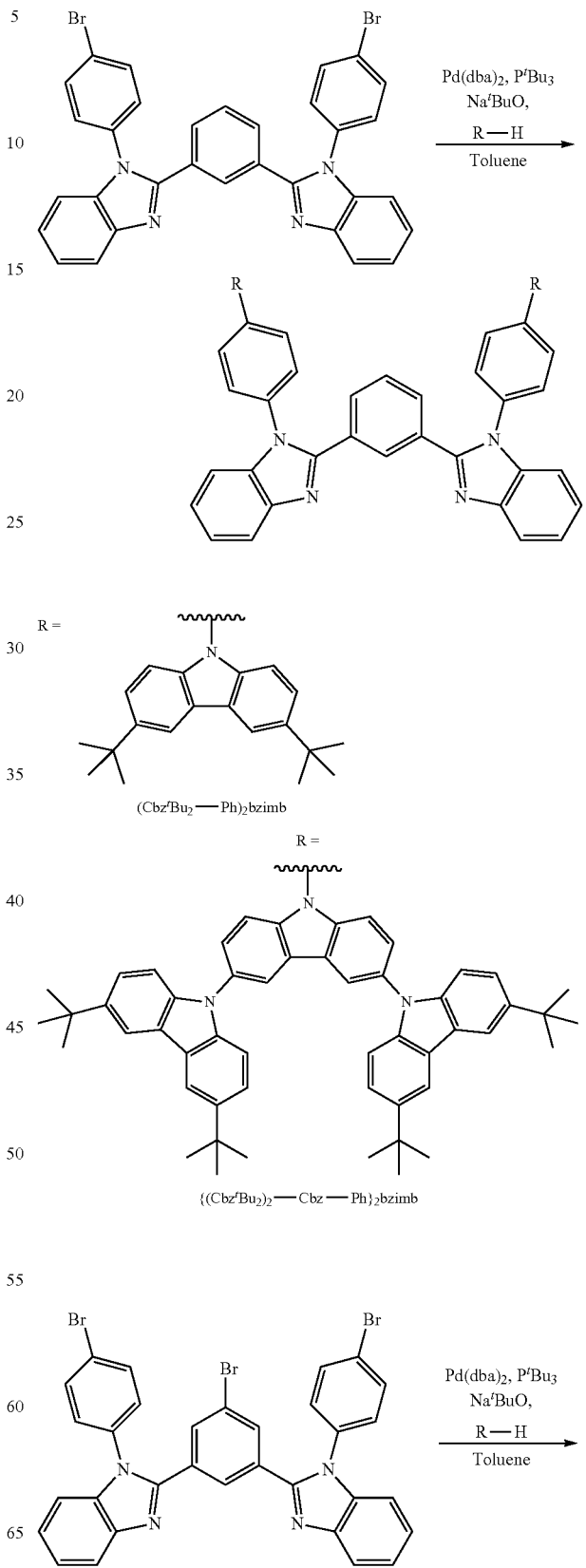

13
-continued

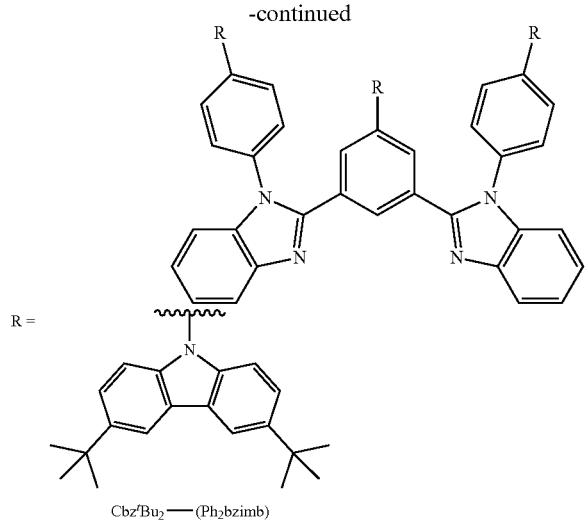

R = Cbz'Bu₂—(Ph₂bzimb)

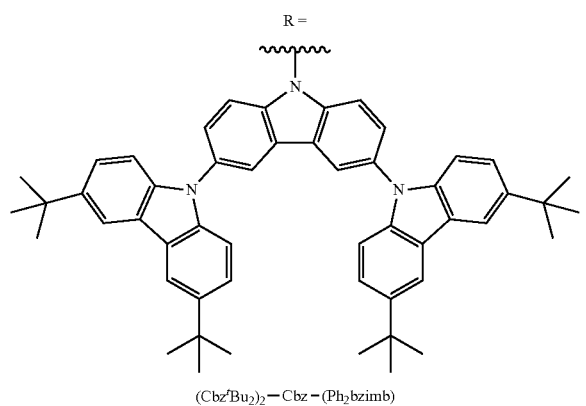

R = (Cbz'Bu₂)₂—Cbz—(Ph₂bzimb)

14

Example 2

Synthesis and Characterization of Platinum(II) Dendrimers 1-14

[Pt{(Cbz$^t$Bu$_2$-Ph)$_2$bzimb}Cl] (compound 1), [Pt({(Cbz$^t$Bu$_2$)$_2$-Cbz-Ph}$_2$bzimb)Cl] (compound 2), [Pt{Cbz$^t$Bu$_2$-(Ph$_2$bzimb)}Cl] (compound 3) and [Pt{(Cbz$^t$Bu$_2$)$_2$-Cbz-(Ph$_2$bzimb)}Cl] (compound 4) were synthesized according to the following methodology. Chloroplatinum(II) compounds 1-4 were synthesized from their respective cyclometalating ligands by the reaction with potassium tetrachloroplatinate(II) in acetic acid and water mixture. For example, to a well-degassed reaction mixture of (Cbz$^t$Bu$_2$-Ph)$_2$bzimb (500 mg, 0.49 mmol) in acetic acid (30 mL) was added a solution of potassium tetrachloroplatinate(II) (225 mg, 0.54 mmol) in deionized water (5 mL). The resulting mixture was stirred and heated to reflux at 150° C. for 48 h. After filtration, the yellow precipitate was washed with water, methanol and diethyl ether. Subsequent recrystallization by diffusing diethyl ether into a concentrated dichloromethane solution of the product gave compound 1 as a yellow solid (308 mg).

Compounds 5-14 were synthesized according to the following methodology. The target compounds were synthesized by the reaction of the respective chloroplatinum(II) compounds with different alkynes in the presence of base and organic solvent. For example, compound 5 was synthesized in a mixture of L1 (100 mg, 0.33 mol) and sodium hydroxide (15 mg, 0.37 mmol) was allowed to stir in degassed methanol solution (5 mL) for 30 minutes. Then a solution of compound 1 (410 mg, 0.33 mmol) in degassed dichloromethane (20 mL) was added and the resultant solution was refluxed for 12 h. After filtration, the yellow precipitate was washed with water (10 mL), methanol (10 mL) and diethyl ether (10 mL). Subsequent recrystallization by diffusing diethyl ether into a concentrated dichloromethane solution (30 mL) of the product gave compound 5 (377 mg) as a yellow solid.

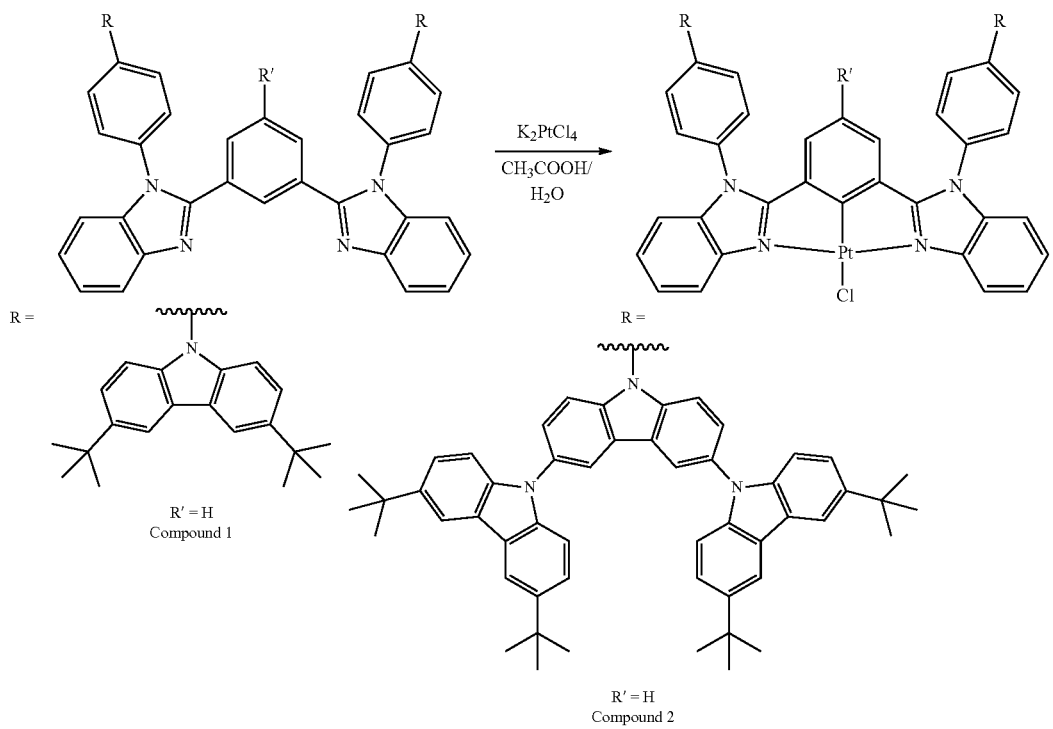

-continued
R' =
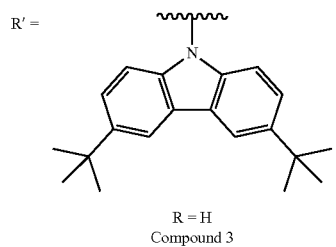
R = H
Compound 3
R' =
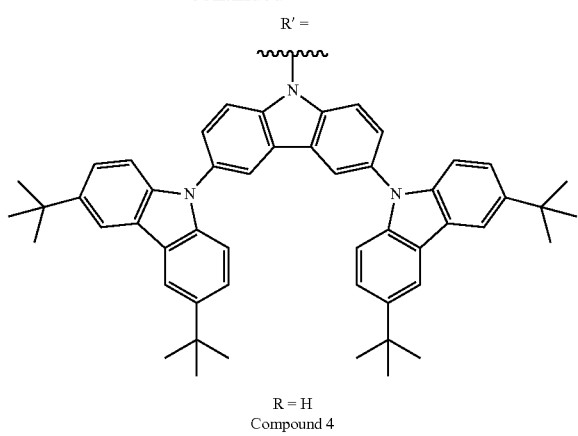
R = H
Compound 4
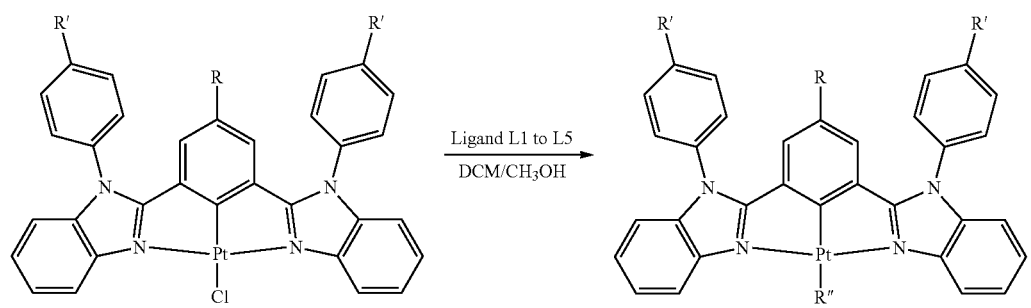
R = H; R' = 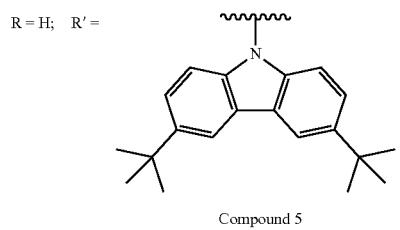 ; R" = Ligand L1
Compound 5
R = H; R' = 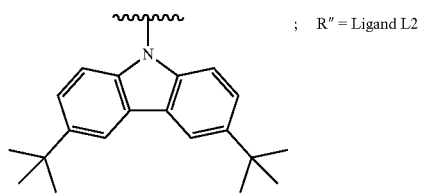 ; R" = Ligand L2
Compound 6
R = H; R' = 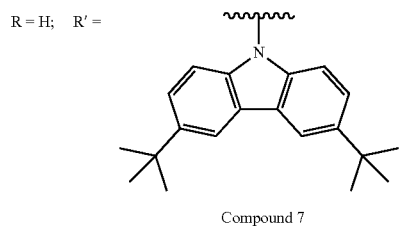 ; R" = Ligand L3
Compound 7
R = H; R' = 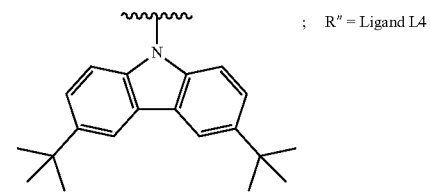 ; R" = Ligand L4
Compound 8
R = H; R' = 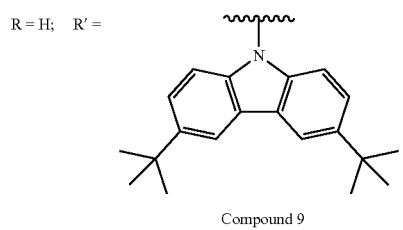 ; R" = Ligand L5
Compound 9
R = H; R' = 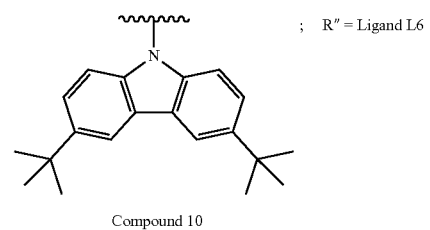 ; R" = Ligand L6
Compound 10

R = H; R' = 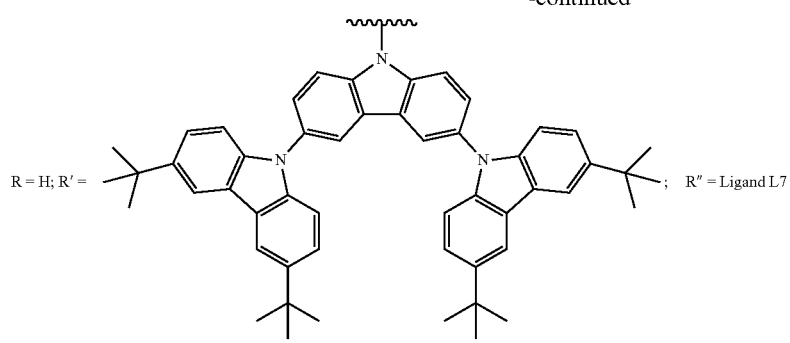 ; R" = Ligand L7
Compound 11
R = 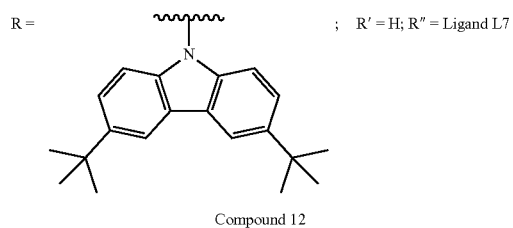 ; R' = H; R" = Ligand L7
Compound 12
R = 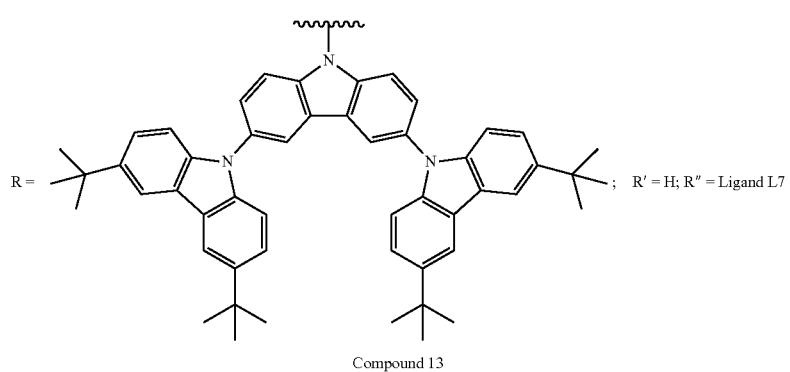 ; R' = H; R" = Ligand L7
Compound 13
R = 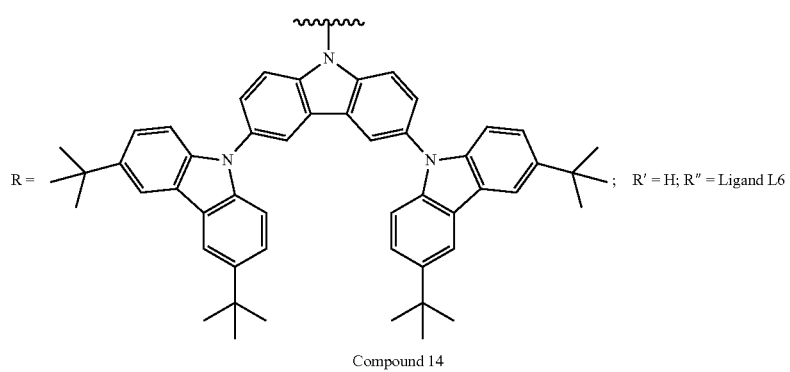 ; R' = H; R" = Ligand L6
Compound 14

-continued
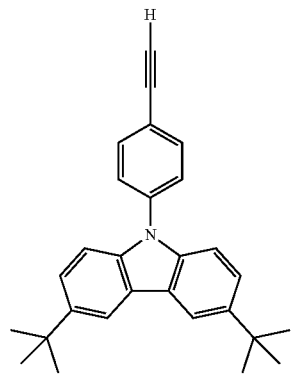
Ligand L1
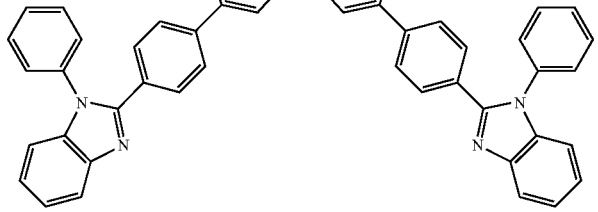
Ligand L2
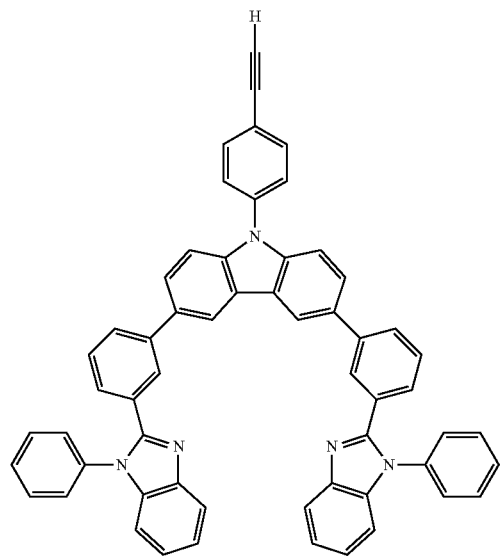
Ligand L3
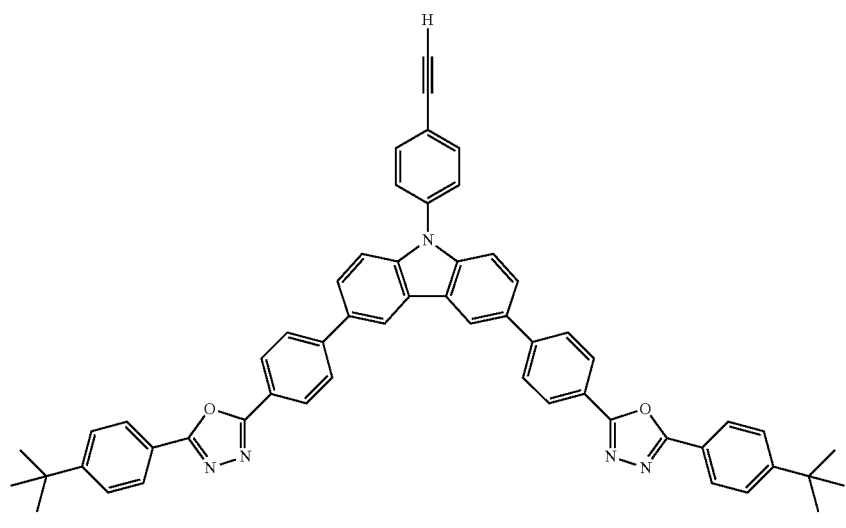
Ligand L4

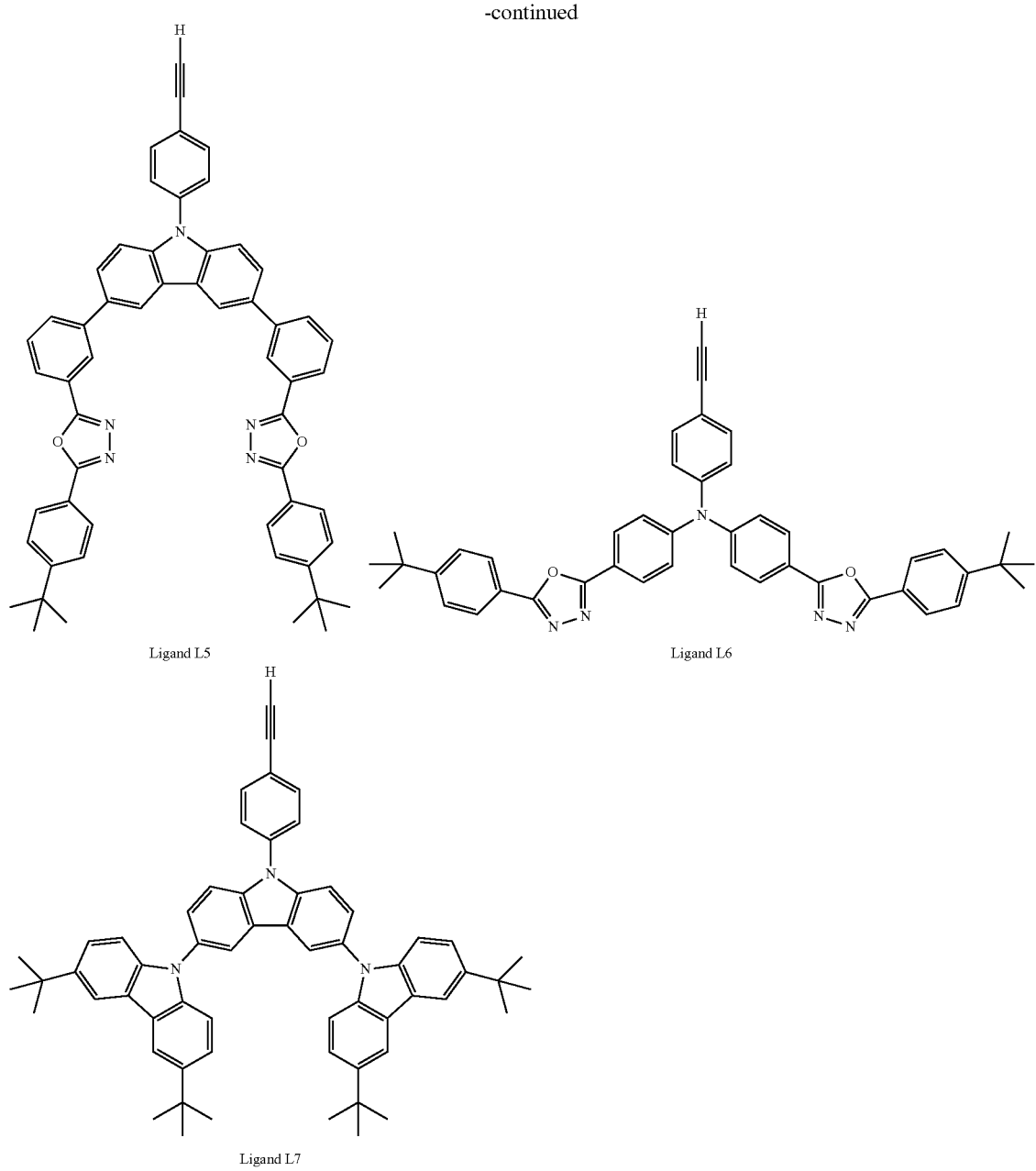

Ligand L5

Ligand L6

Ligand L7

$^1$H NMR spectra were recorded on a Bruker AVANCE 400 (400 MHz) Fourier-transform NMR spectrometer with chemical shifts reported relative to tetramethylsilane. Positive FAB mass spectra were recorded on a Thermo Scientific DFS High Resolution Magnetic Sector Mass Spectrometer. High-resolution ESI mass spectra were recorded on a Bruker maXis II™ High Resolution LC-QTOF Mass Spectrometer. IR spectra were recorded as KBr disk on a Bio-Rad FTS-7 FTIR spectrometer (4000-400 cm$^{-1}$). Elemental analyses for the metal complexes were performed on the Carlo Erba 1106 elemental analyzer at the Institute of Chemistry, Chinese Academy of Sciences in Beijing. The satisfactory results of the characteristic analyses show the high purity of all compounds 1-14. The characteristic spectral properties of compounds 1-14 are as follows.

Compound 1 [Pt{(Cbz$^t$Bu$_2$-Ph)$_2$bzimb}Cl]. Yield: 308 mg, 45%. $^1$H NMR (400 MHz, CDCl$_3$, 298 K, relative to Me$_4$Si): δ 1.49 (s, 36H, tert-butyl protons), 6.61 (d, J=8.0 Hz, 2H, phenyl protons), 6.85 (t, J=8.0 Hz, 1H, phenyl proton), 7.29 (d, J=7.8 Hz, 2H, benzimidazolyl protons), 7.41 (t, J=7.8 Hz, 2H, benzimidazolyl protons), 7.52-7.55 (m, 10H, benzimidazolyl and carbazolyl protons), 7.81 (d, J=8.5 Hz, 4H, phenyl protons), 7.94 (d, J=8.5 Hz, 4H, phenyl protons), 8.19 (d, J=1.0 Hz, 4H, carbazolyl protons), 9.22 (d, J=7.8 Hz, 2H, benzimidazolyl protons). Positive FAB-MS: m/z 1210 [M-Cl]$^+$. Elemental analyses: Found (%): C, 69.25; H, 5.72; N, 6.48. Calcd for C$_{72}$H$_{67}$N$_6$PtCl: C, 69.36; H, 5.42; N, 6.74.

Compound 2 [Pt({(Cbz$^t$Bu$_2$)$_2$-Cbz-Ph}$_2$bzimb)Cl]. Yield: 220 mg, 80%. $^1$H NMR (400 MHz, CDCl$_3$, 298 K, relative to Me$_4$Si): δ 1.46 (s, 72H, tert-butyl protons), 6.78 (d, J=8.0 Hz, 2H, phenyl protons), 6.96 (t, J=8.0 Hz, 1H, phenyl proton), 7.31 (d, J=7.8 Hz, 2H, benzimidazolyl protons), 7.34 (d, J=8.6 Hz, 8H, carbazolyl protons), 7.44-7.46 (m, 10H, benzimidazolyl and carbazolyl protons), 7.58 (t, J=7.8 Hz, 2H, benzimidazolyl protons), 7.70 (dd, J=8.6 and 1.0 Hz, 4H, carbazolyl protons), 7.84 (d, J=8.6 Hz, 4H, carbazolyl protons), 7.99 (d, J=8.6 Hz, 4H, phenyl protons), 8.11-8.15 (m, 12H, carbazolyl and phenyl protons), 8.29 (d, J=1.0 Hz, 4H, carbazolyl protons), 9.28 (d, J=7.8 Hz, 2H, benzimidazolyl protons). Positive FAB-MS: m/z 2095 [M-Cl]$^+$. Elemental analyses: Found (%): C, 74.54; H, 6.30; N, 6.24. Calcd for $C_{136}H_{127}N_{10}PtCl \cdot 3H_2O$: C, 74.72; H, 6.13; N, 6.41.

Compound 3 [Pt{Cbz$^t$Bu$_2$-(Ph$_2$bzimb)}Cl]. Yield: 220 mg, 80%. $^1$H NMR (400 MHz, CD$_2$Cl$_2$, 298 K, relative to Me$_4$Si): δ 1.47 (s, 18H, tert-butyl protons), 6.65 (s, 2H, phenyl protons), 7.02 (d, J=8.6 Hz, 2H, carbazolyl protons), 7.21 (d, J=8.2 Hz, 2H, benzimidazolyl protons), 7.39-7.47 (m, 6H, benzimidazolyl and carbazolyl protons), 7.54 (t, J=8.2 Hz, 2H, benzimidazolyl protons), 7.57-7.64 (m, 8H, benzimidazolyl and phenyl protons), 8.05 (d, J=1.8 Hz, 2H, carbazolyl protons), 9.10 (d, J=8.2 Hz, 2H, benzimidazolyl protons). Positive FAB-MS: m/z 933 [M-Cl]$^+$. Elemental analyses: Found (%): C, 63.85; H, 4.44; N, 7.12. Calcd for $C_{52}H_{44}N_5PtCl \cdot 5H_2O$: C, 63.83; H, 4.64; N, 7.16.

Compound 4 [Pt{(Cbz$^t$Bu$_2$)$_2$-Cbz-(Ph$_2$bzimb)}Cl]. Yield: 220 mg, 80%. $^1$H NMR (400 MHz, CDCl$_3$, 298 K, relative to Me$_4$Si): δ 1.48 (s, 36H, tert-butyl protons), 6.78 (s, 2H, phenyl protons), 7.17 (d, J=8.2 Hz, 2H, benzimidazolyl protons), 7.30 (d, J=8.6 Hz, 4H, carbazolyl protons), 7.35 (d, J=8.6 Hz, 2H, carbazolyl protons), 7.38 (t, J=8.2 Hz, 2H, benzimidazolyl protons), 7.49 (dd, J=8.6 and 1.8 Hz, 4H, carbazolyl protons), 7.54-7.57 (m, 6H, benzimidazolyl, carbazolyl and phenyl protons), 7.76-7.78 (m, 8H, phenyl protons), 8.15 (d, J=1.8 Hz, 2H, carbazolyl protons), 8.18 (d, J=1.8 Hz, 4H, carbazolyl protons), 9.21 (d, J=8.2 Hz, 2H, benzimidazolyl protons). Positive FAB-MS: m/z 1376 [M-Cl]$^+$. Elemental analyses: Found (%): C, 70.58; H, 5.20; N, 6.81. Calcd for $C_{84}H_{74}N_7PtCl \cdot H_2O$: C, 70.55; H, 5.36; N, 6.86.

Compound 5 [Pt{(Cbz$^t$Bu$_2$-Ph)$_2$bzimb}(Ligand 1)]. Yield: 377 mg, 72%. $^1$H NMR (400 MHz, CDCl$_3$, 298 K, relative to Me$_4$Si, δ 1.49 (s, 54H, tert-butyl protons), 6.72 (d, J=7.8 Hz, 2H, benzimidazolyl protons), 6.86 (t, J=7.8 Hz, 1H, benzimidazolyl proton), 7.31 (d, J=8.0 Hz, 2H, benzimidazolyl protons), 7.42 (t, J=8.0 Hz, 2H, benzimidazolyl protons), 7.35 (d, J=8.7 Hz, 4H, carbazolyl protons), 7.48 (dd, J=8.7 and 1.9 Hz, 4H, carbazolyl protons), 7.72 (dd, J=8.7 and 1.9 Hz, 2H, carbazolyl protons), 7.78-7.81 (m, 8H, carbazolyl and phenyl protons), 7.91-7.96 (m, 8H, phenyl protons), 8.17 (d, J=1.1 Hz, 4H, carbazolyl protons), 8.19 (s, 2H, carbazolyl protons), 9.28 (d, J=8.0 Hz, 2H, benzimidazolyl protons). Positive FAB-MS: m/z 1589 [M]$^+$. IR (KBr disk): 2089 cm$^{-1}$ ν(C≡C). Elemental analyses: Found (%): C, 74.62; H, 6.33; N, 6.10. Calcd for $C_{100}H_{95}N_7Pt \cdot H_2O$: C, 74.69; H, 6.08; N, 6.10.

Compound 6 [Pt{(Cbz$^t$Bu$_2$-Ph)$_2$bzimb}(Ligand 2)]. Yield: 196 mg, 75%. $^1$H NMR (400 MHz, CDCl$_3$, 298 K, relative to Me$_4$Si): δ 1.49 (s, 36H, tert-butyl protons), 6.73 (d, J=8.0 Hz, 2H, phenyl protons of (Cbz$^t$Bu$_2$-Ph)$_2$bzimb), 6.87 (t, J=8.0 Hz, 1H, phenyl proton of (Cbz$^t$Bu$_2$-Ph)$_2$bzimb), 7.31-7.39 (m, 6H, phenyl and benzimidazolyl protons of —C≡C—C$_6$H$_4$-Cbz-(PBI-4)$_2$), 7.41-7.45 (m, 6H, carbazolyl and benzimidazolyl protons of (Cbz$^t$Bu$_2$-Ph)$_2$bzimb), 7.52-7.58 (m, 18H, phenyl and benzimidazolyl protons of —C≡C—C$_6$H$_4$-Cbz-(PBI-4)$_2$, carbazolyl protons of (Cbz$^t$Bu$_2$-Ph)$_2$bzimb), 7.60-7.63 (m, 4H, carbazolyl protons of —C≡C—C$_6$H$_4$-Cbz-(PBI-4)$_2$ and benzimidazolyl protons of (Cbz$^t$Bu$_2$-Ph)$_2$bzimb), 7.72 (s, 8H, phenyl protons of (Cbz$^t$Bu$_2$-Ph)$_2$bzimb), 7.74 (dd, J=8.3 and 1.6 Hz, 2H, carbazolyl protons of —C≡C—C$_6$H$_4$-Cbz-(-PBI-4)$_2$), 7.85 (d, J=8.6 Hz, 4H, phenyl protons of —C≡C—C$_6$H$_4$-Cbz-(PBI-4)$_2$, 7.92-7.99 (m, 8H, phenyl and benzimidazolyl protons of —C≡C—C$_6$H$_4$-Cbz-(PBI-4)$_2$, benzimidazolyl protons of (Cbz$^t$Bu$_2$-Ph)$_2$bzimb), 8.19 (d, J=1.6 Hz, 4H, carbazolyl protons of (Cbz$^t$Bu$_2$-Ph)$_2$bzimb), 8.44 (d, J=1.6 Hz, 2H, carbazolyl protons of —C≡C—C$_6$H$_4$-Cbz-(PBI-4)$_2$), 9.28 (d, J=8.0 Hz, 2H, benzimidazolyl protons of (Cbz$^t$Bu$_2$-Ph)$_2$bzimb). HRMS (positive ESI) found 2014.8128 [M+H]$^+$; calcd for $C_{130}H_{104}N_{11}Pt$ (m/z): 2014.8147. IR(KBr disk): 2085 cm$^{-1}$ ν(C≡C). Elemental analyses: Found (%): C, 70.53; H, 4.84; N, 6.94. Calcd for $C_{130}H_{103}N_{11}Pt \cdot 2CHCl_3$: C, 70.37; H, 4.70; N, 6.84.

Compound 7 [Pt{(Cbz$^t$Bu$_2$-Ph)$_2$bzimb}(Ligand 3)]. Yield: 208 mg, 83%. $^1$H NMR (400 MHz, CD$_2$Cl$_2$, 298 K, relative to Me$_4$Si): δ 1.50 (s, 36H, tert-butyl protons), 6.85 (d, J=8.0 Hz, 2H, phenyl protons of (Cbz$^t$Bu$_2$-Ph)$_2$bzimb), 6.96 (t, J=8.0 Hz, 1H, phenyl proton of (Cbz$^t$Bu$_2$-Ph)$_2$bzimb), 7.31-7.39 (m, 6H, phenyl and benzimidazolyl protons of —C≡C—C$_6$H$_4$-Cbz-(PBI-3)$_2$), 7.41-7.45 (m, 6H, carbazolyl and benzimidazolyl protons), 7.52-7.58 (m, 18H, phenyl, carbazolyl and benzimidazolyl), 7.60-7.63 (m, 4H, carbazolyl protons and benzimidazolyl protons), 7.72 (s, 8H, phenyl protons), 7.74 (dd, J=8.3 and 1.6 Hz, 2H, carbazolyl protons), 7.85 (d, J=8.6 Hz, 4H, phenyl protons), 7.92-7.99 (m, 8H, phenyl and benzimidazolyl protons), 8.19 (d, J=1.6 Hz, 4H, carbazolyl protons), 8.44 (d, J=1.6 Hz, 2H, carbazolyl protons), 9.28 (d, J=8.0 Hz, 2H, benzimidazolyl protons). HRMS (positive ESI) found 2014.8018 [M+H]$^+$; calcd for $C_{130}H_{104}N_{11}Pt$ (m/z): 2014.8147. IR(KBr disk): 2085 cm$^{-1}$ ν(C≡C). Elemental analyses: Found (%): C, 74.94; H, 5.26; N, 7.36. Calcd for $C_{130}H_{103}N_{11}Pt \cdot CH_2Cl_2$: C, 74.95; H, 5.04; N, 7.34.

Compound 8 [Pt{(Cbz$^t$Bu$_2$-Ph)$_2$bzimb}(Ligand 4)]. Yield: 202 mg, 80%. $^1$H NMR (400 MHz, CDCl$_3$, 298 K, relative to Me$_4$Si): δ 1.39 (s, 18H, tert-butyl protons), 1.49 (s, 36H, tert-butyl protons), 6.73 (d, J=8.0 Hz, 2H, phenyl protons), 6.88 (t, J=8.0 Hz, 1H, phenyl proton), 7.33 (d, J=7.9 Hz, 2H, benzimidazolyl protons), 7.45 (t, J=7.9 Hz, 2H, benzimidazolyl protons of (Cbz$^t$Bu$_2$-Ph)$_2$bzimb), 7.56-7.66 (m, 16H, benzimidazolyl, carbazolyl and phenyl protons), 7.70 (d, J=8.5 Hz, 2H, carbazolyl protons), 7.82-7.87 (m, 6H, carbazolyl and phenyl protons), 7.95-7.98 (m, 8H, phenyl proton) 8.02 (d, J=8.2 Hz, 2H, phenyl protons), 8.12 (d, J=8.4 Hz, 4H, phenyl protons), 8.20 (d, J=1.7 Hz, 4H, carbazolyl protons), 8.28 (d, J=8.4 Hz, 4H, phenyl protons), 8.56 (d, J=1.7 Hz, 2H, carbazolyl protons), 9.29 (d, J=7.9 Hz, 2H, benzimidazolyl protons of (Cbz$^t$Bu$_2$-Ph)$_2$bzimb). HRMS (positive ESI) found 2030.8533 [M+H]$^+$; calcd for $C_{128}H_{112}N_{11}O_2Pt$ (m/z):2030.8671. IR(KBr disk): 2085 cm$^{-1}$ ν(C≡C). Elemental analyses: Found (%): C, 71.82; H, 5.31; N, 7.25. Calcd for $C_{128}H_{111}N_{11}O_2Pt \cdot CHCl_3$: C, 72.07; H, 5.25; N, 7.17.

Compound 9 [Pt{(Cbz$^t$Bu$_2$-Ph)$_2$bzimb}(Ligand 5)]. Yield: 212 mg, 84%. $^1$H NMR (400 MHz, CD$_2$Cl$_2$, 298 K, relative to Me$_4$Si): δ 1.39 (s, 18H, tert-butyl protons), 1.50 (s, 36H, tert-butyl protons), 6.86 (d, J=7.5 Hz, 2H, phenyl protons), 6.88 (t, J=7.5 Hz, 1H, phenyl proton), 7.41 (d, J=8.0 Hz, 2H, benzimidazolyl protons), 7.50 (t, J=8.0 Hz, 2H, benzimidazolyl protons), 7.57-7.63 (m, 12H, carbazolyl and phenyl protons), 7.66 (t, J=8.0 Hz, 2H, benzimidazolyl protons), 7.71-7.76 (m, 6H, carbazolyl and phenyl protons of), 7.91 (m, 6H, carbazolyl and phenyl protons), 7.99-8.05 (m, 8H, phenyl protons), 8.12-8.17 (m, 6H, phenyl protons), 8.23 (d, J=1.8 Hz, 4H, carbazolyl protons), 8.61 (d, J=1.8 Hz, 2H, phenyl protons), 8.67 (d, J=1.8 Hz, 2H, carbazolyl protons), 9.24 (d, J=8.0 Hz, 2H, benzimidazolyl protons). HRMS (positive ESI) found 2030.8534 [M+H]$^+$; calcd for $C_{128}H_{112}N_{11}O_2Pt$ (m/z): 2030.8671. IR(KBr disk): 2085 cm$^{-1}$ ν(C≡C). Elemental analyses: Found (%): C, 73.81; H, 5.40; N, 7.33. Calcd for $C_{128}H_{111}N_{11}O_2Pt \cdot 5CHCl_3$: C, 73.84; H, 5.38; N, 7.37.

Compound 10 [Pt{(Cbz$^t$Bu$_2$-Ph)$_2$bzimb}(Ligand 6)]. Yield: 210 mg, 83%. $^1$H NMR (400 MHz, CDCl$_3$, 298 K, relative to Me$_4$Si): δ 1.39 (s, 18H, tert-butyl protons), 1.49

(s, 36H, tert-butyl protons), 6.71 (d, J=7.7 Hz, 2H, phenyl protons), 6.71 (d, J=7.7 Hz, 1H, phenyl proton), 7.25 (d, J=8.6 Hz, 2H, phenyl protons), 7.30 (d, J=8.0 Hz, 2H, benzimidazolyl protons), 7.35 (d, J=8.6 Hz, 4H, phenyl protons), 7.41 (t, J=8.0 Hz, 2H, benzimidazolyl protons), 7.55-7.58 (m, 14H, benzimidazolyl carbazolyl protons and phenyl protons), 7.64 (d, J=8.6 Hz, 4H, phenyl protons), 7.73 (d, J=8.6 Hz, 2H, phenyl protons), 7.80 (d, J=8.6 Hz, 4H, phenyl protons of), 7.84 (d, J=8.6 Hz, 4H, phenyl protons), 7.95 (d, J=8.6 Hz, 4H, phenyl protons), 8.10 (d, J=8.6 Hz, 4H, phenyl protons), 8.19 (d, J=1.8 Hz, 4H, carbazolyl protons), 8.22 (d, J=8.6 Hz, 4H, phenyl protons), 9.27 (d, J=8.0 Hz, 2H, benzimidazolyl protons). Positive FAB-MS: m/z 2031 [M]$^+$. IR(KBr disk): 2083 cm$^{-1}$ v(C≡C). Elemental analyses: Found (%): C, 74.20; H, 5.53; N, 7.47. Calcd for $C_{128}H_{113}N_{11}O_2Pt·0.5CH_2Cl_2$: C, 74.38; H, 5.54; N, 7.43.

Compound 11 [Pt{(Cbz$^t$Bu$_2$-Ph)$_2$bzimb}(Ligand 7)]. Yield: 500 mg, 52%. $^1$H NMR (400 MHz, CDCl$_3$, 298 K, relative to Me$_4$Si): δ 1.46 (s, 72H, tert-butyl protons), 1.48 (s, 36H, tert-butyl protons), 6.90 (d, J=7.7 Hz, 2H, phenyl protons), 6.98 (t, J=7.7 Hz, 1H, phenyl proton), 7.35 (d, J=8.6 Hz, 8H, carbazolyl protons), 7.38 (d, J=8.6 Hz, 4H, carbazolyl protons), 7.45-7.49 (m, 14H, benzimidazolyl and carbazolyl protons), 7.64-7.69 (m, 4H, benzimidazolyl and carbazolyl protons), 7.71 (dd, J=8.6 and 1.4 Hz, 4H, carbazolyl protons), 7.77 (d, J=8.1 Hz, 2H, phenyl protons), 7.80 (d, J=8.6 Hz, 2H, carbazolyl protons), 7.85 (d, J=8.6 Hz, 4H, carbazolyl protons), 8.03 (d, J=8.1 Hz, 4H, phenyl protons), 8.07 (d, J=8.1 Hz, 2H, phenyl protons), 8.13-8.19 (m, 18H, benzimidazolyl, carbazolyl and phenyl protons), 8.27 (d, J=1.4 Hz, 2H, carbazolyl protons), 8.29 (d, J=1.4 Hz, 4H, carbazolyl protons), 9.34 (d, J=7.7 Hz, 2H, benzimidazolyl protons). Positive FAB-MS: m/z 2915 [M]$^+$. IR (KBr disk): 2083 cm$^{-1}$ v(C≡C). Elemental analyses: Found (%): C, 77.10; H, 6.41; N, 5.91. Calcd for $C_{196}H_{185}N_{13}Pt·CH_2Cl_2$: C, 77.02; H, 6.17; N, 5.90.

Compound 12 [Pt{(Cbz$^t$Bu$_2$-Ph)$_2$bzimb}(Ligand 7)]. Yield: 370 mg, 64%. $^1$H NMR (400 MHz, CDCl$_3$, 298 K, relative to Me$_4$Si): δ 1.47 (s, 18H, tert-butyl protons), 1.48 (s, 36H, tert-butyl protons), 6.68 (s, 2H, phenyl protons), 7.01 (d, J=8.6 Hz, 2H, phenyl protons), 7.19 (d, J=8.3 Hz, 2H, benzimidazolyl protons), 7.37-7.43 (m, 10H, benzimidazolyl, carbazolyl and phenyl protons), 7.48 (dd, J=8.7 and 1.4 Hz, 4H, carbazolyl protons), 7.54-7.62 (m, 10H, benzimidazolyl, carbazolyl and phenyl protons), 7.66 (dd, J=8.7 and 1.4 Hz, 2H, carbazolyl protons), 7.75 (d, J=8.5 Hz, 2H, phenyl protons), 7.79 (d, J=8.7 Hz, 2H, carbazolyl protons), 8.03 (d, J=1.4 Hz, 2H, carbazolyl protons), 8.05 (d, J=8.5 Hz, 2H, phenyl protons), 8.17 (d, J=1.4 Hz, 4H, carbazolyl protons), 8.26 (d, J=1.4 Hz, 2H, carbazolyl protons), 9.26 (d, J=8.3 Hz, 2H, benzimidazolyl protons). Positive FAB-MS: m/z 1754 [M]$^+$. IR (KBr disk): 2089 cm$^{-1}$ v(C≡C). Elemental analyses: Found (%): C, 74.56; H, 5.65; N, 6.30. Calcd for $C_{112}H_{102}N_8Pt·5CHCl_3$: C, 74.45; H, 5.69; N, 6.17.

Compound 13 [Pt{(Cbz$^t$Bu$_2$-Ph)$_2$bzimb}(Ligand 7)]. Yield: 406 mg, 56%. $^1$H NMR (400 MHz, CDCl$_3$, 298 K, relative to Me$_4$Si): δ 1.48 (s, 36H, tert-butyl protons), 1.49 (s, 36H, tert-butyl protons), 6.88 (s, 2H, phenyl protons), 7.23 (d, J=8.3 Hz, 2H, benzimidazolyl protons), 7.32 (d, J=8.6 Hz, 4H, carbazolyl protons), 7.37-7.40 (m, 6H, carbazolyl protons), 7.43 (t, J=8.3 Hz, 2H, benzimidazolyl protons), 7.47-7.51 (m, 8H, carbazolyl protons), 7.55-7.58 (m, 4H, carbazolyl and phenyl protons), 7.62-7.72 (m, 12H, benzimidazolyl, carbazolyl and phenyl protons), 7.77 (d, J=8.5 Hz, 2H, phenyl protons), 7.80 (d, J=8.1 Hz, 2H, carbazolyl protons), 8.07 (d, J=8.5 Hz, 2H, phenyl protons), 8.16-8.19 (m, 10H, carbazolyl protons), 8.27 (d, J=1.4 Hz, 2H, carbazolyl protons), 9.30 (d, J=8.3 Hz, 2H, benzimidazolyl protons). Positive FAB-MS: m/z 2196 [M]$^+$. IR (KBr disk): 2083 cm$^{-1}$ v(C≡C). Elemental analyses: Found (%): C, 77.40; H, 6.18; N, 6.08. Calcd for $C_{144}H_{132}N_{10}Pt·2H_2O$: C, 77.43; H, 6.14; N, 6.27.

Compound 14 [Pt{(Cbz$^t$Bu$_2$-Ph)$_2$bzimb}(Ligand 6)]. Yield: 205 mg, 78%. $^1$H NMR (400 MHz, CDCl$_3$, 298 K, relative to Me$_4$Si): δ 1.39 (s, 18H, tert-butyl protons), 1.48 (s, 36H, tert-butyl protons), 6.86 (d, J=7.5 Hz, 2H, phenyl protons), 7.20 (d, J=8.0 Hz, 2H, benzimidazolyl protons), 7.25 (d, J=8.5 Hz, 2H, phenyl protons), 7.31 (d, J=8.6 Hz, 4H, carbazolyl protons), 7.34-7.41 (m, 10H, benzimidazolyl and phenyl protons) 7.49 (dd, J=8.6 and 1.8 Hz, 4H, carbazolyl protons), 7.54-7.60 (m, 10H, benzimidazolyl, carbazolyl and phenyl protons), 7.63-7.69 (m, 10H, carbazolyl and phenyl protons), 7.74 (d, J=8.5 Hz, 2H, phenyl protons), 7.80 (d, J=8.5 Hz, 4H, phenyl protons), 8.15 (d, J=1.8 Hz, 2H, carbazolyl protons), 8.18 (d, J=1.8 Hz, 4H, carbazolyl protons), 8.22 (d, J=8.5 Hz, 4H, phenyl protons), 9.28 (d, J=8.0 Hz, 2H, benzimidazolyl protons). Positive FAB-MS: m/z 2194 [M]$^+$. IR (KBr disk): 2083 cm$^{-1}$ v(C≡C). Elemental analyses: Found (%): C, 75.56; H, 5.48; N, 7.52. Calcd for $C_{140}H_{120}N_{12}O_2Pt·1.5H_2O$: C, 75.59; H, 5.57; N, 7.56.

Scheme 1

Compound 1

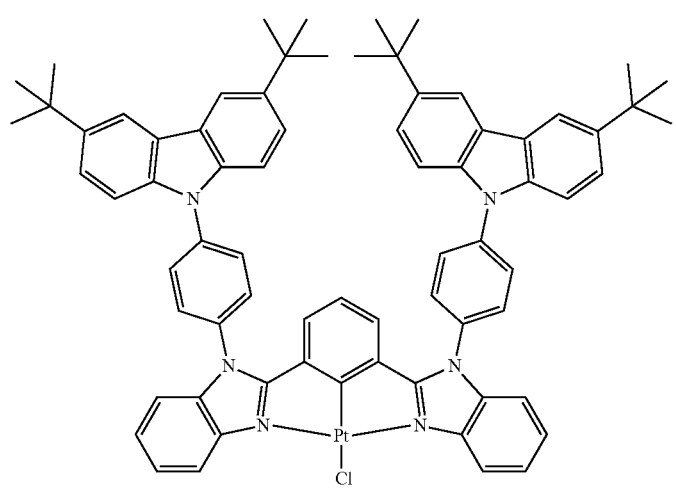

-continued
Compound 2
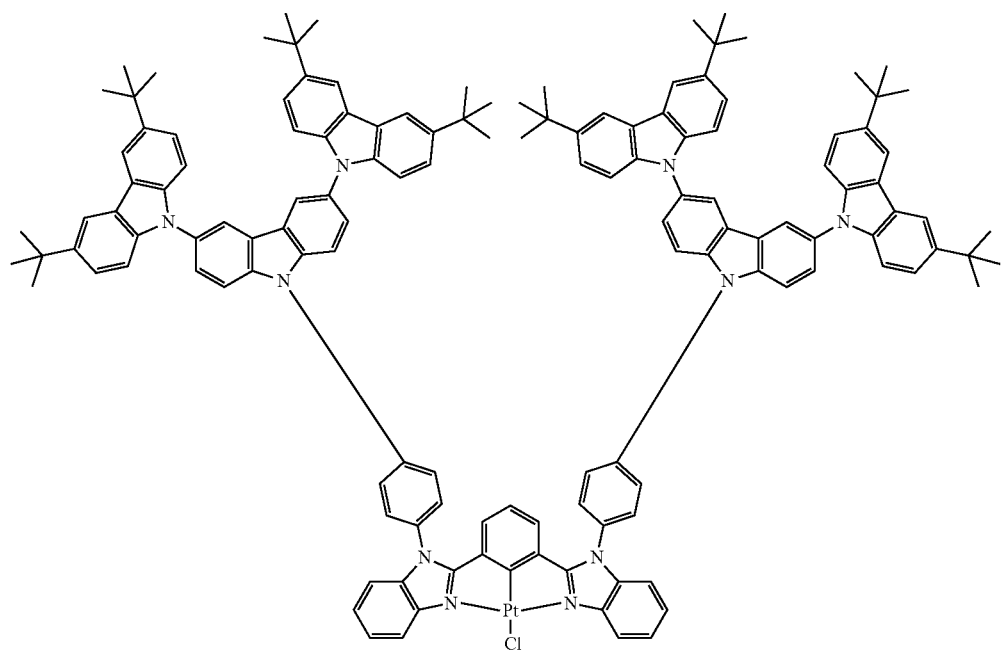
Compound 3
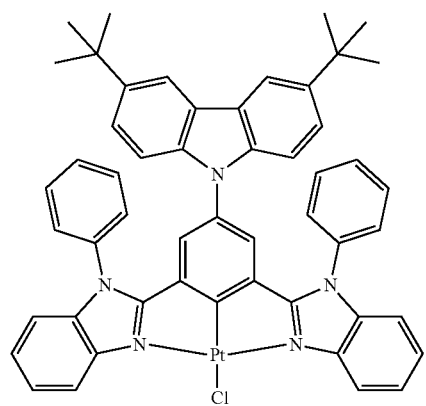
Compound 4
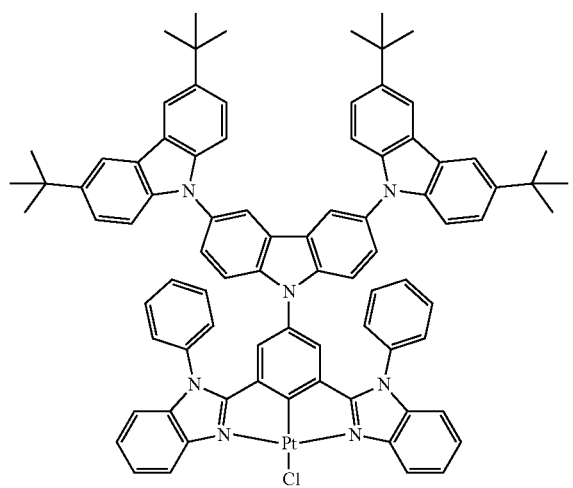

Compound 5
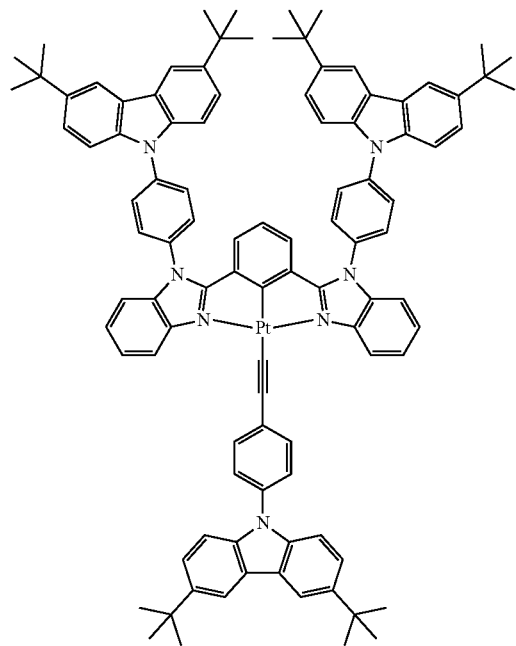
Compound 6
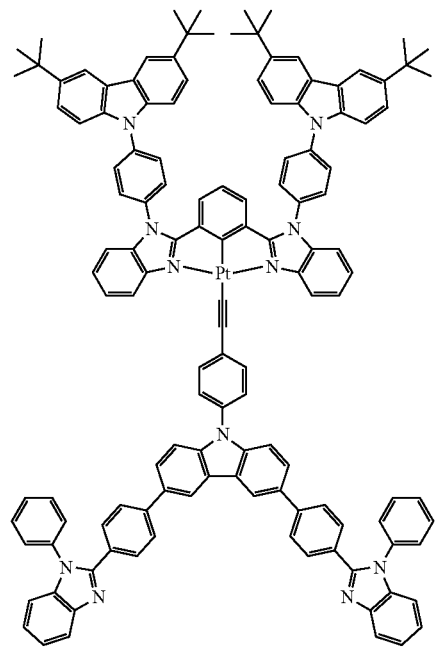
Compound 7
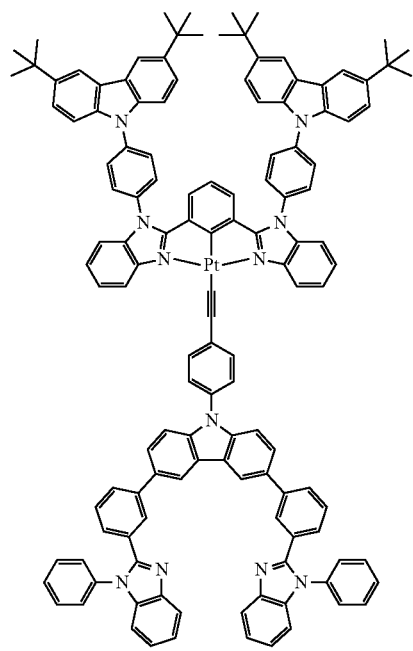
Compound 8
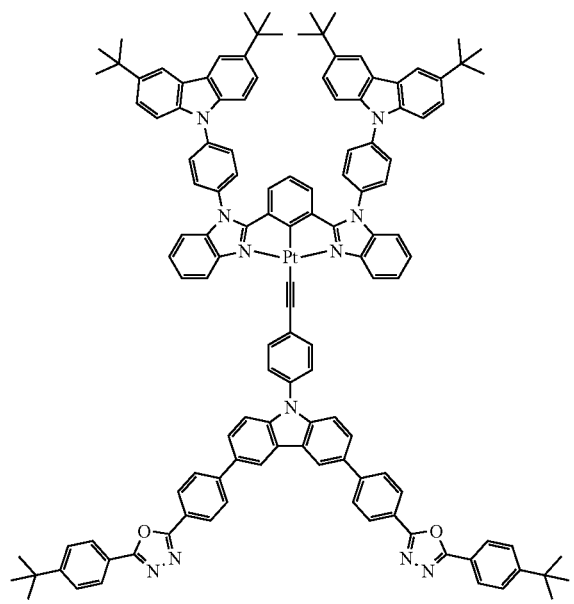

Compound 9
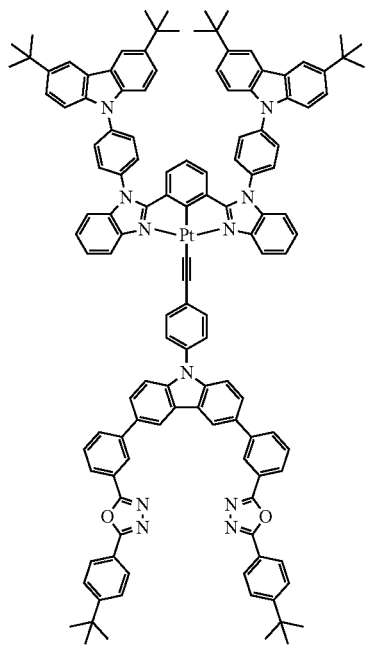
Compound 10
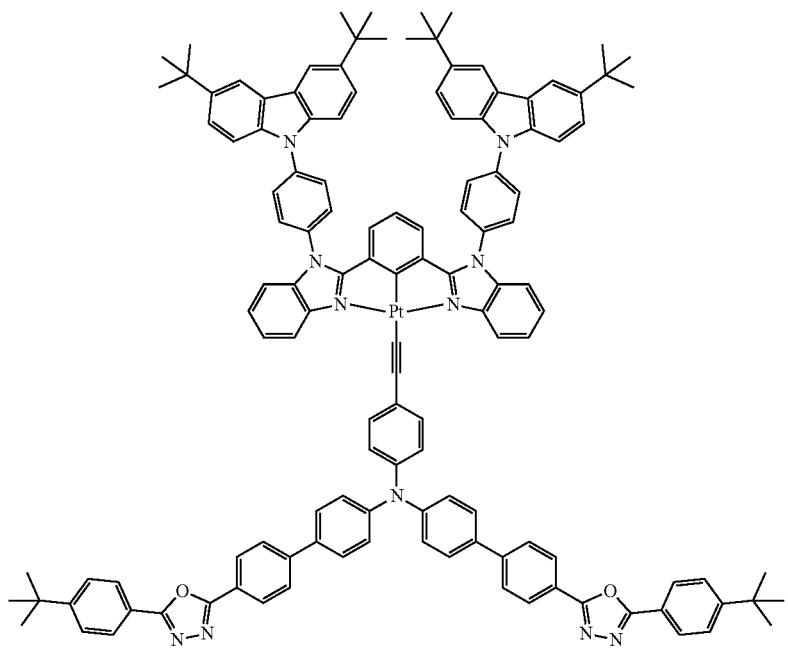

-continued
Compound 11
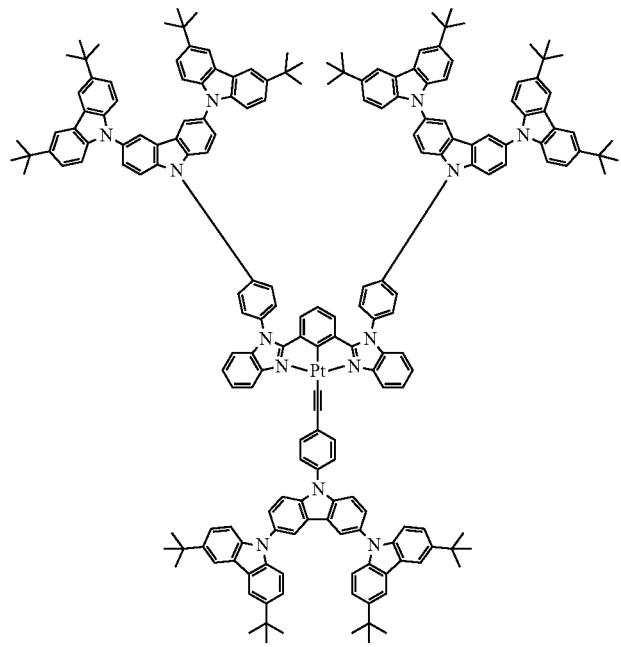
Compound 12
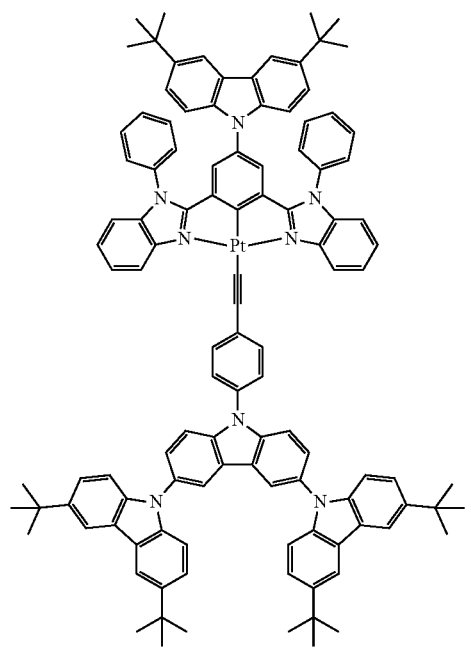
Compound 13
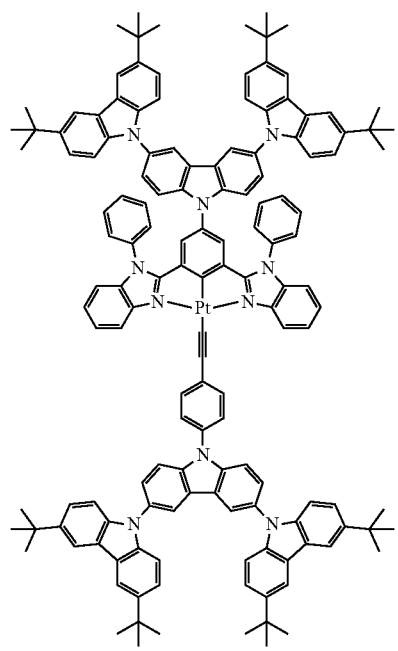

Compound 14

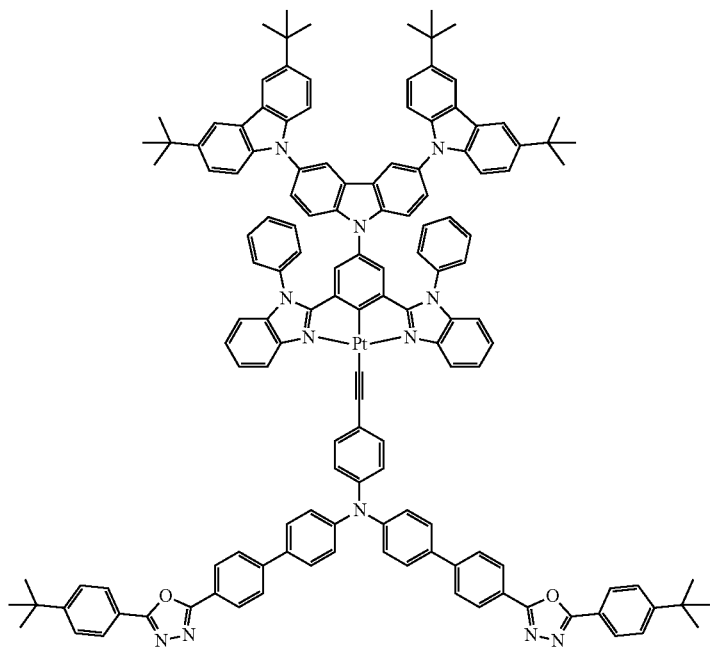

Example 3

UV-Vis Absorption Properties

The UV-vis absorption spectra of compounds 1-14 in dichloromethane solution at 298 K show intense vibronic-structured absorption bands at 283-330 nm and moderately intensevibronic-structured absorption bands at 345-480 nm. The UV-vis absorption data are summarized in Table 1.

Figure 2:
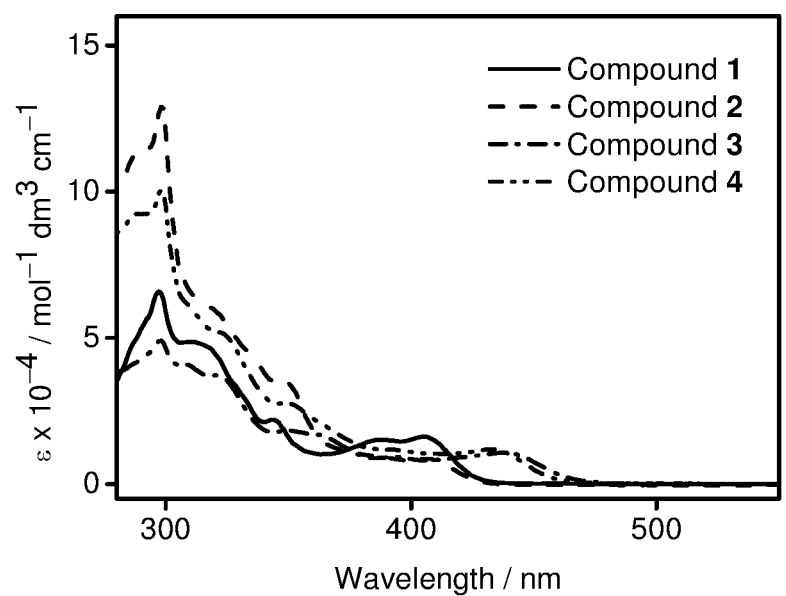
FIG. 2 shows the UV-vis absorption spectra of compounds 1-4 in dichloromethane at 298 K.
Figure 3:
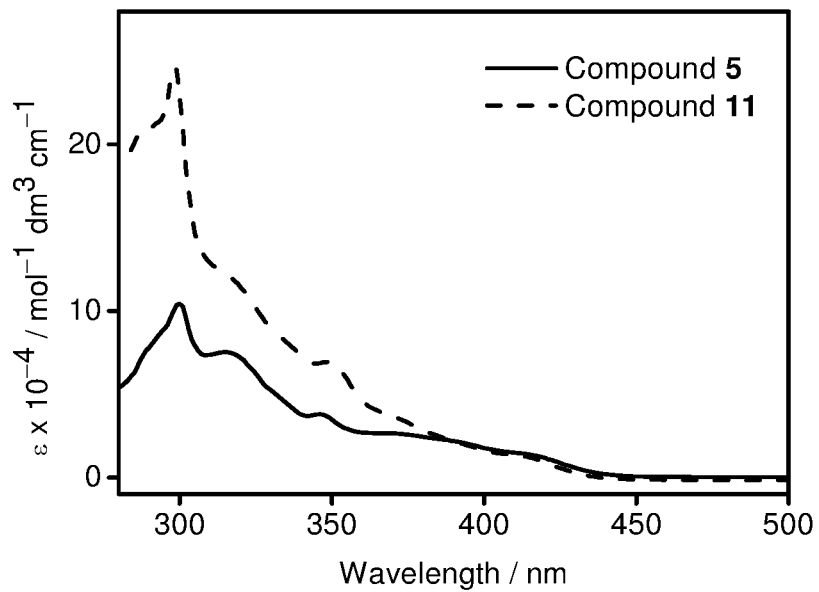
FIG. 3 shows the UV-vis absorption spectra of compounds 5 and 11 in dichloromethane at 298 K.
Figure 4:
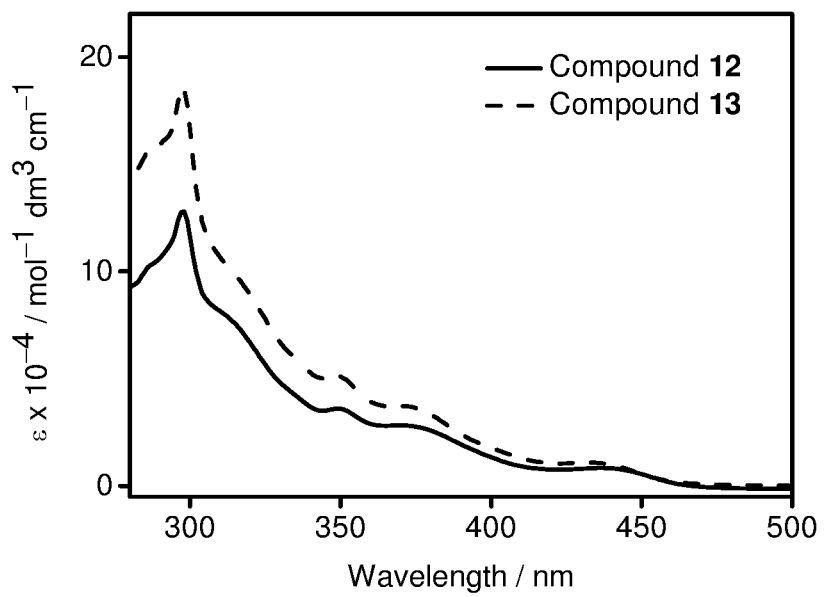
FIG. 4 shows the UV-vis absorption spectra of compounds 12 and 13 in dichloromethane at 298 K.

FIG. 2 depicts the UV-vis absorption spectra for compounds 1-4. The higher-energy absorptions for compounds 1-4 are assigned to spin-allowed intraligand (IL) π→π* transitions of the cyclometalated bzimb ligands and carbazole units. The lower-energy absorptions are attributed to IL π-π* transitions of the cyclometalated bzimb ligands, with substantial mixing of metal-to-ligand charge transfer (MLCT) [dπ(Pt)→π*(bzimb)]. The higher-energy absorption bands for compounds 5, 11-13 at 280-330 nm are assigned to spin-allowed IL π→π* transitions of the cyclometalated bzimb ligands and carbazole units, with the molar extinction coefficients increasing with the number of carbazole units in the complexes. This trend can be seen in the comparison between compounds 5 and 11 as shown in FIG. 3 and compounds 12 and 13 as shown in FIG. 4. The lower-energy absorption bands are attributed to IL π→π* transitions of the cyclometalated bzimb ligands, with substantial mixing of MLCT [dπ(Pt)→π*(bzimb)] and ligand-to-ligand charge transfer (LLCT) [π(C≡C—R)→π*(bzimb)] characters, as supported by the insensitivity towards the choice of the alkynes. However, it is found that this lower-energy absorption band is sensitive to the substitution on the 5-position of the bzimb ligands. A significant red-shift is observed for compounds 12 and 13 which contain carbazole dendrimers at the 5-position of the bzimb ligand compared with the other complexes without substituents as shown in FIG. 4. Such red shifts could be rationalized by the direct incorporation of the carbazole dendrimers at the 5-position of the bzimb ligand, which is connected through the electron-donating nitrogen atom. This would lead to the destabilization of the HOMO energy level relative to the lowest unoccupied molecular orbital (LUMO) energy level for compounds 12 and 13, thus narrowing the HOMO-LUMO energy gap, leading to a red shift in the transition energy.

Figure 5:
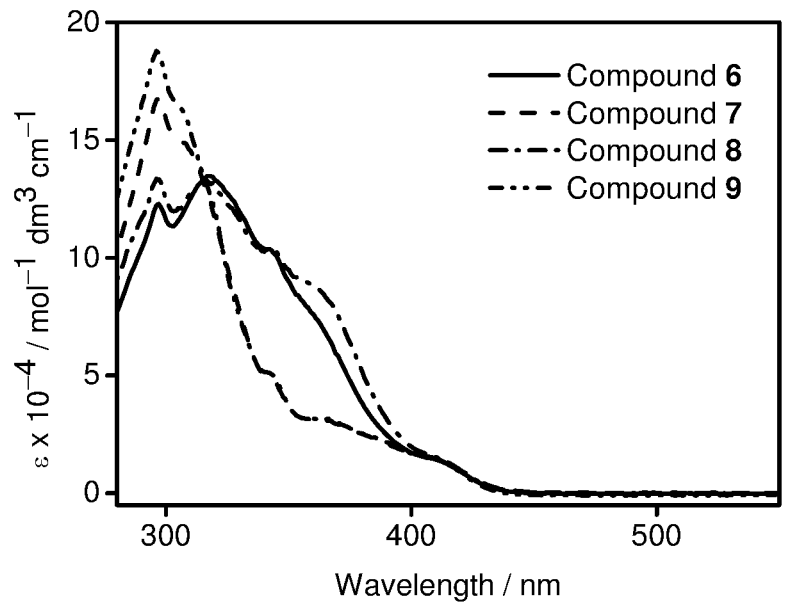
FIG. 5 shows the UV-vis absorption spectra of compounds 6-9 in dichloromethane at 298 K.
Figure 6:
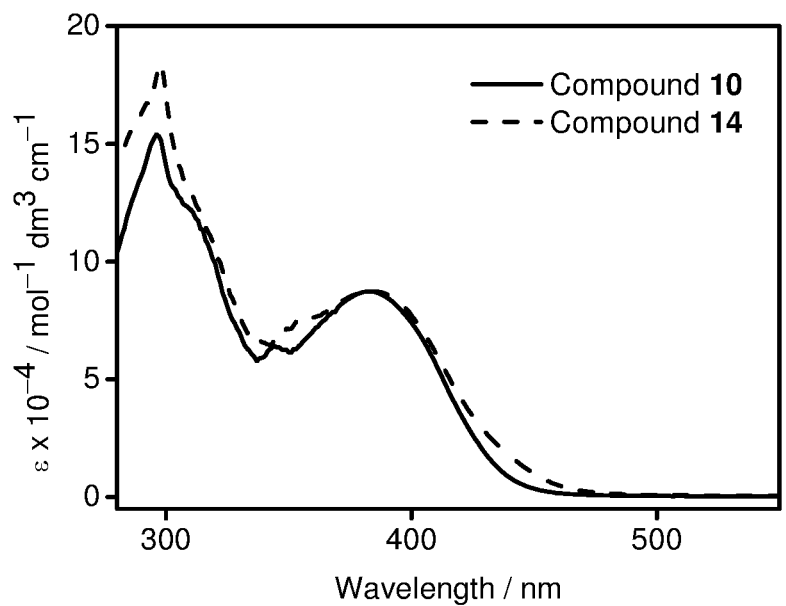
FIG. 6 shows the UV-vis absorption spectra of compounds 10 and 14 in dichloromethane at 298 K.

FIGS. 5 and 6 depict the UV-vis absorption spectra for compounds 6-10 and 14. Compounds 6-10 and 14 show intense vibronic-structured absorption bands at 290-340 nm with a moderately intense vibronic-structured band at 365-410 nm. The absorption bands at λ≤300 nm are attributed to the spin-allowed IL π→π* transitions of the carbazole or triphenylamine and bzimbunits, whereas the lower-energy absorption bands at ca. 305-390 nm could be assigned as the π→π* transitions from the electron-donating carbazole or triphenylamine moiety to the electron-accepting phenylbenzimidazole or oxadiazole moiety, mixing with the IL π→π* transitions of the cyclometalated bzimb ligand. By weakening the π-conjugation between the donor and acceptor moieties via meta-substitution instead of the para-substitution, a blue shift of the charge transfer band is observed when comparing compound 6 (352 nm) with compound 7 (305 nm), as well as comparing compound 8 (363 nm) with compound 9 (307 nm), as shown in FIG. 5. In addition, the transition energies of these charge transfer bands are found to be dependent on the nature of the electron-donating and accepting units. A red-shifted absorption band is observed from compound 6 (352 nm) to compound 8 (363 nm) which bear phenylbenzimidazole and oxadiazole units respectively as observed in FIG. 5. Significant red shift is also noticed when comparing the triphenylamine containing compound 6 (383 nm) to the carbazole-containing compound 7 (363 nm). This can be rationalized by the higher-lying HOMO level of triphenylamine than that of carbazole as shown in FIGS. 5 and 6. The lower-energy absorptions beyond 390 nm are attributed to IL π→π* transitions of the bzimb ligand, with substantial mixing of MLCT [dπ(Pt)→π*(bzimb)] and LLCT [π(C≡C—R)→π*(bzimb)] character.

Example 4

Photoluminescence Properties

Figure 7:
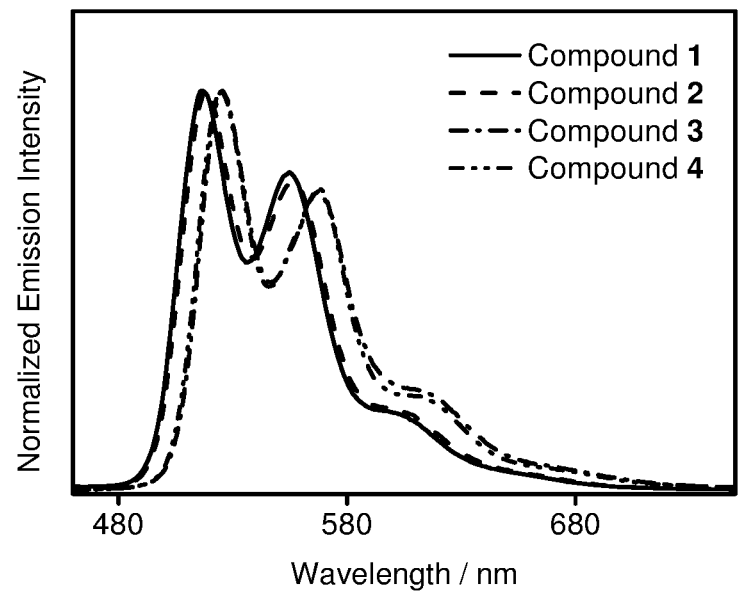
FIG. 7 shows the normalized photoluminescence spectra of compounds 1-4 in dichloromethane at 298 K.
Figure 8:
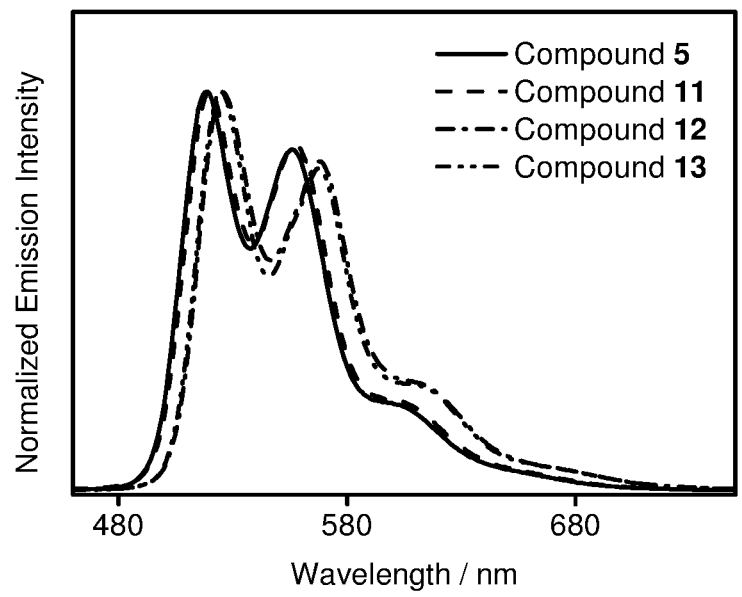
FIG. 8 shows the normalized photoluminescence spectra of compounds 5 and 11-13 in dichloromethane at 298 K.
Figure 9:
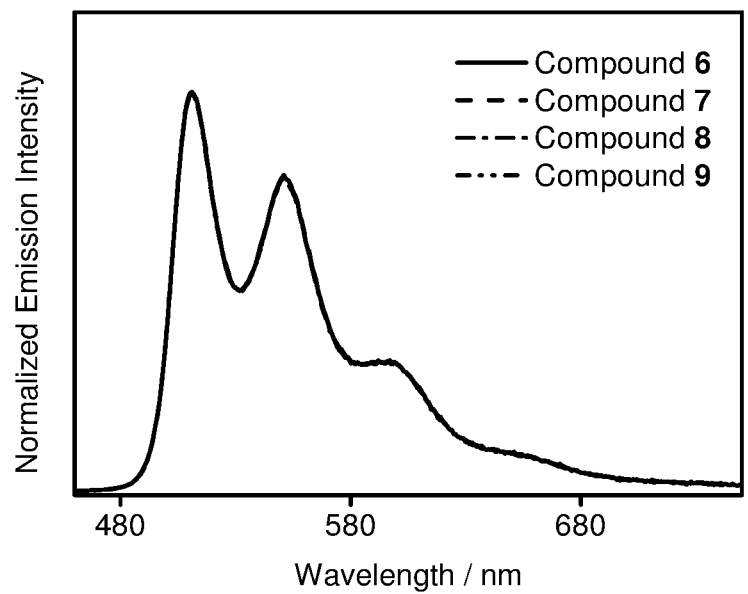
FIG. 9 shows the normalized photoluminescence spectra of compounds 6-9 in dichloromethane at 298 K.
Figure 10:
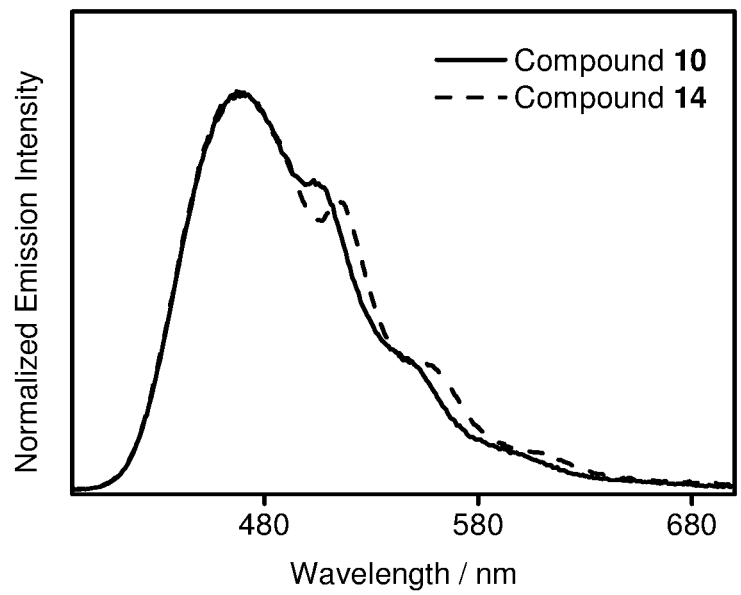
FIG. 10 shows the normalized photoluminescence spectra of compounds 10 and 14 in dichloromethane at 298 K.

In degassed dichloromethane solution, compounds 1-9 and 11-13 show a vibronic-structured emission band with emission maxima at ca. 511-530 nm, and progressional spacings of about 1300 cm$^{-1}$, corresponding to typical aromatic vibrational modes of the bzimb-based ligands as shown in FIGS. 7-9. The emission has been assigned to be originated from the $^3$IL[π→π*(bzimb)]/MLCT[dπ(Pt)→π*(bzimb)] excited state, as supported by the insensitivity of the emission band towards the choice of the alkynes. The emission energy is found to be sensitive to the substitution on the 5-position of the bzimb ligands. A red shift of the emission band with emission maxima at 530 nm is observed for compounds 12 and 13 as shown in FIG. 7. The introduction of dendritic carbazole moiety at the 5-position of the bzimb ligand which is connected through the electron-donating nitrogen atom would raise the energy of the HOMO level to a larger extent than that of the LUMO level, similar to the UV-vis absorption studies. This would therefore lead to the red-shift in energy. FIG. 10 displays the photoluminescence spectra for compounds 10 and 14 in dichloromethane at 298 K. A dual-emissive behavior has been observed for compounds 10 and 14. Apart from the $^3$IL emission similar to the other compounds, an additional higher-energy structureless emission at ca. 468 nm is found. This band could be assigned as the intramolecular charge transfer excited state ($^1$ICT) of the triphenylamine-oxadiazole donor-acceptor pair on the alkynes.

Figure 11:
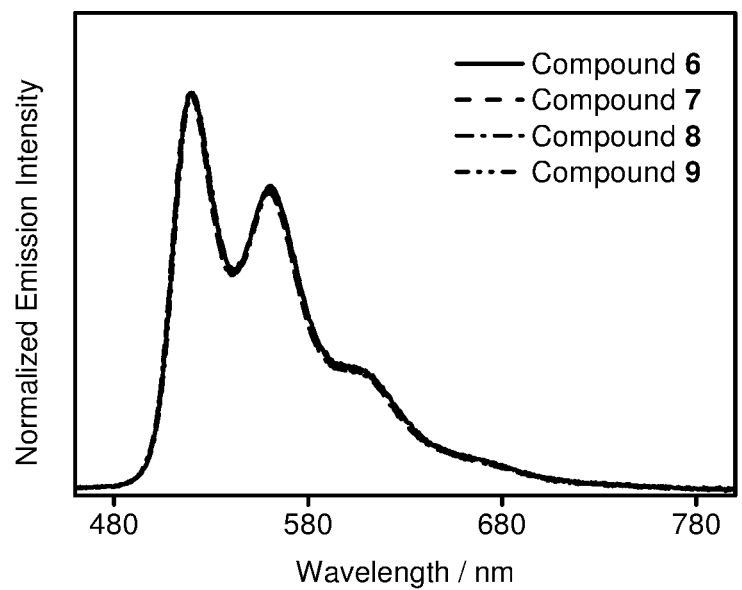
FIG. 11 shows the normalized photoluminescence spectra of thin films of 20 wt % compounds 6-9 doped into 4,4',4"-tris(carbazol-9-yl)triphenylamine (TCTA) 2,7-bis(diphenylphosphoryl)-9,9'-spirobifluorene (SPPO13) (1:1) at 298 K.
Figure 12:
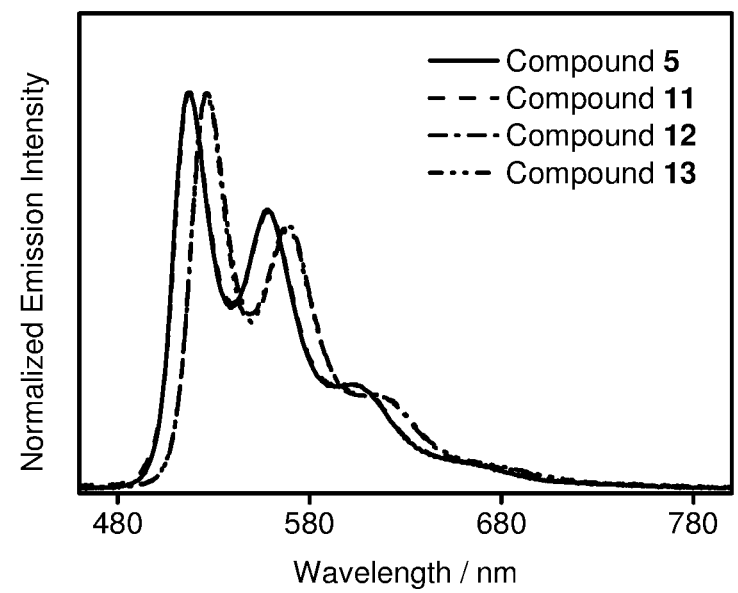
FIG. 12 shows the normalized photoluminescence spectra of thin films of 5 wt % compounds 5 and 11-13 doped into 1,3-bis(carbazol-9-yl)benzene (MCP) at 298 K.

FIG. 11 depicts the thin-film emission spectra of 20 wt % compounds 6-9 doped in mixed host consisting of TCTA:SPPO13 (1:1), whereas FIG. 12 shows the thin-film emission spectra of 5 wt % compounds 5, 11-13 doped in MCP. The emission spectra are almost identical to their corresponding emission spectra in solution without undesirable emission from the host materials, indicating the complete energy transfer from the host materials to the guest complexes.

TABLE 1

Photophysical data for compounds 1-14

| Compound | Medium (T/K) | Absorption $\lambda_{max}$/nm ($\varepsilon$/dm$^3$mol$^{-1}$cm$^{-1}$) | Emission $\lambda_{max}$/nm ($\tau_0$/μs) | $\Phi_{sol}$ | $\Phi_{film}$ |
|---|---|---|---|---|---|
| 1 | CH$_2$Cl$_2$ (298) | 287 (48360), 297 (65310), 313 (48360), 344 (22310), 386 (15910), 405 (16460) | 517, 555, 600 (6.0) | 0.34[a] | 0.74[c] |
| 2 | CH$_2$Cl$_2$ (298) | 287 (112995), 298 (128500), 318 (60290), 349 (31580), 380 (10290), 407 (9130) | 517, 555, 600 (5.8) | 0.48[a] | 0.54[c] |
| 3 | CH$_2$Cl$_2$ (298) | 298 (49070), 308 (40990), 322 (36960), 352 (18300), 393 (9270), 440 (10800) | 525, 567, 616 (3.1) | 0.55[a] | 0.68[c] |
| 4 | CH$_2$Cl$_2$ (298) | 298 (100060), 323 (51880), 349 (27630), 392 (11750), 433 (11750) | 525, 567, 616 (3.3) | 0.69[a] | 0.79[c] |
| 5 | CH$_2$Cl$_2$ (298) | 290 (79780), 300 (104160), 316 (75820), 346 (38490), 390 (22565), 414 (14650) | 518, 556, 600 (5.7) | 0.47[a] | 0.83[c] |
| 6 | CH$_2$Cl$_2$ (298) | 297 (121970), 318 (134385), 342 (103920), 352 (84960), 412 (13650) | 511, 550, 595 (3.3) | 0.49[a] | 0.47[d] |
| 7 | CH$_2$Cl$_2$ (298) | 297 (167070), 305 (147940), 342 (50900), 365 (31705), 412 (13650) | 511, 550, 595 (3.3) | 0.59[a] | 0.62[d] |
| 8 | CH$_2$Cl$_2$ (298) | 297 (133250), 316 (131570), 343 (103320), 363 (85560), 412 (13650) | 511, 550, 595 (3.6) | 0.64[a] | 0.63[d] |
| 9 | CH$_2$Cl$_2$ (298) | 297 (187940), 307 (162030), 342 (50900), 365 (31705), 412 (13650) | 511, 550, 595 (3.5) | 0.59[a] | 0.65[d] |
| 10 | CH$_2$Cl$_2$ (298) | 296 (153220), 310 (121910), 353 (73390), 383 (86880), 433 (14550) | 468, 504, 549, 595 (<0.1, 3.8)[e] | 0.60[b] | 0.42[c] |
| 11 | CH$_2$Cl$_2$ (298) | 287 (208510), 298 (245840), 317 (122330), 350 (69615), 384 (26520), 414 (13480) | 520, 558, 602 (6.2) | 0.54[a] | 0.59[c] |
| 12 | CH$_2$Cl$_2$ (298) | 297 (126770), 310 (81420), 350 (36140), 373 (27650), 440 (7080) | 526, 565, 610 (5.8) | 0.64[a] | 0.76[c] |

TABLE 1-continued

Photophysical data for compounds 1-14

| Compound | Medium (T/K) | Absorption $\lambda_{max}$/nm ($\varepsilon$/dm$^3$mol$^{-1}$cm$^{-1}$) | Emission $\lambda_{max}$/nm ($\tau_0$/µs) | $\Phi_{sol}$ | $\Phi_{film}$ |
|---|---|---|---|---|---|
| 13 | CH$_2$Cl$_2$ (298) | 297 (184820), 313 (101290), 349 (51020), 373 (37550), 438 (10660) | 525, 568, 607 (6.5) | 0.64[a] | 0.65[c] |
| 14 | CH$_2$Cl$_2$ (298) | 297 (182900), 309 (132160), 338 (58750), 384 (87420), 440 (17790) | 468, 515, 558, 610 (<0.1, 2.8)[e] | 0.56[b] | 0.65[d] |

[a]The luminescence quantum yield, measured at room temperature using [Ru(bpy)$_3$]Cl$_2$ in aqueous state as the reference (excitation wavelength = 436 nm, $\Phi_{lum}$ = 0.042)
[b]The luminescence quantum yield, measured at room temperature using quinine sulphate in 1.0N H$_2$SO$_4$ as the reference (excitation wavelength = 366 nm, $\Phi_{lum}$ = 0.546)
[c]$\Phi_{film}$ of Pt(II) compounds doped into MCP excited at wavelength of 300 nm
[d]$\Phi_{film}$ of Pt(II) compounds doped into TCTA:SPPO13 (1:1) excited at wavelength of 300 nm
[e]Biexponential decay Example 5

An organic EL device according to an embodiment of the invention was constructed in the following manner:
a) A transparent anode ITO-coated borosilicate glass substrate (38 mm×38 mm) with sheet resistance of 30Ω per square was ultrasonicated in the commercial detergent Decon 90, rinsed in deionized water having a resistivity of 18.2 mega-ohm for 15 minutes, and then dried in an oven at 120 degree C. for an hour. The substrate was next subjected to an UV-ozone treatment in a Jelight 42-220 UVO-Cleaner equipped with a mercury grid lamp for 15 minutes in order to increase the work function of the ITO-coated glass substrate for better hole injection into the organic layer;
b) A 70-nm thick PEDOT:PSS hole-transporting layer was spin-coated by using a Laurell WS-400Ez-6NPP-Lit2 single wafer spin processor at 7000 rpm from 30 seconds onto the ITO-coated glass substrate of step a and baked at 110 degree C. for 10 minutes in air;
c) A 60-nm thick light-emitting layer was spin-coated by using a Laurell WS-400Ez-6NPP-Lit2 single wafer spin processor at 6000 rpm from 25 seconds onto the PEDOT:PSS layer of step b and baked at 80 degree C. for 10 minutes in air, in which compound 6 was doped into light-emitting TCTA:SPPO13 (1:1) layer at different concentrations in the range from 5 to 50 wt %;
d) The substrate was put into a vacuum chamber, and the chamber was pumped down from 1 bar to 5×10$^{-6}$ mbar;
e) A 30-nm thick BmPyPhB electron-transporting layer was deposited by thermal evaporation onto the light-emitting layer of step c.
f) A 0.8-nm thick LiF layer and a 80 nm thick Al layer were deposited by thermal evaporation on BmPyPhB of step e to form an electron-injecting cathode.

All materials were prepared by thermal evaporation from tantalum boats by applying current through the tantalum boats. Deposition rates were monitored with a quartz oscillation crystal and a Sigma SQM-242 quartz crystal card and controlled at 0.1-0.2 nm s$^{-1}$ for both organic and metal layers. Current density-voltage-luminance characteristics of organic EL devices were measured with a programmable Keithley model 2420 power source and a Spectrascan PR 655 colorimeter under ambient air conditions.

Example 6

The same materials and processing procedures were employed as described in Example 5, except that compounds 7-9 were doped into TCTA:SPPO13 as light-emitting layer.

Figure 13:
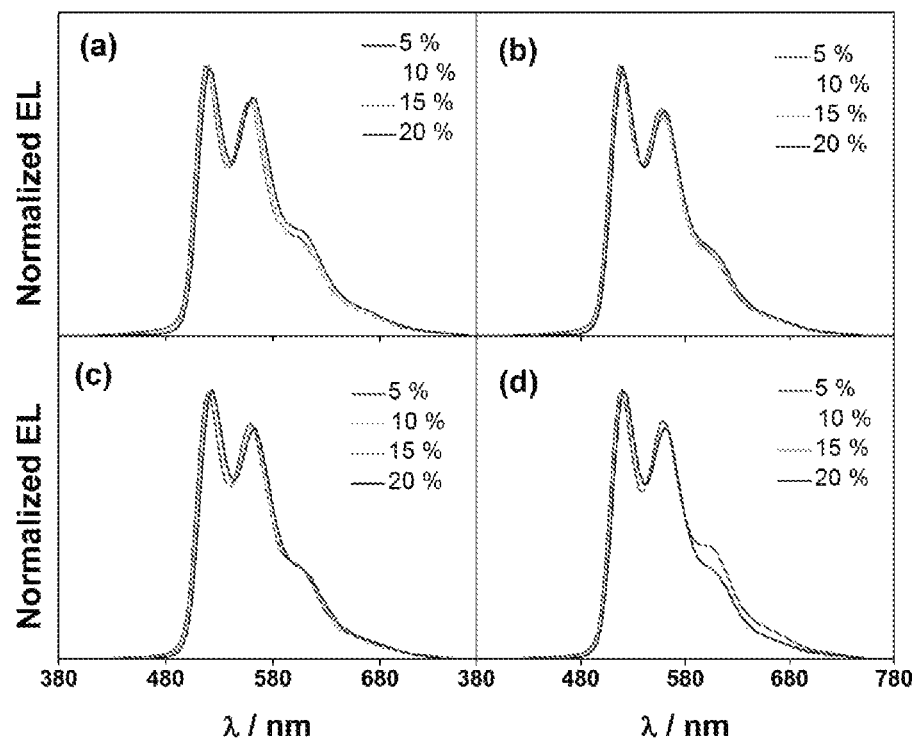
FIG. 13 shows the normalized EL spectra of solution-processable OLEDs made with (a) 6, (b) 7, (c) 8 and (d) 9 doped with different concentrations.

FIG. 13 depicts the normalized EL spectra of the devices at a current density of 20 mA cm$^{-2}$. All the devices exhibit vibronic-structured emission, and the EL spectra for all the devices are exactly identical to their emission spectra in solution. Notably, the full-width-at-half-maxima of all the devices remain unchanged upon increasing the dopant concentration from 5 wt % to 20 wt %. In addition, both x and y chromaticity coordinates of all the devices are only varied by less than 0.02. This concentration-independent EL suggests the low tendency of the bipolar platinum(II) complexes to form aggregates through Pt . . . Pt and/or π-π stacking in the thin films, in excellent agreement with the photoluminescence studies.

Figure 14:
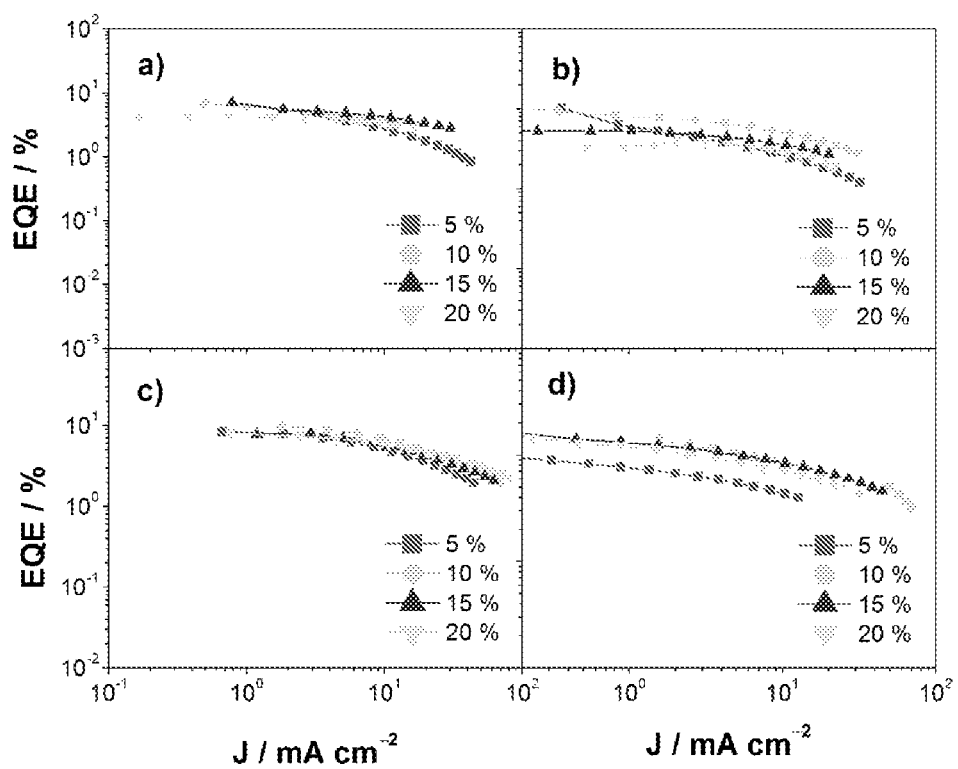
FIG. 14 shows the EQEs of solution-processable OLEDs made with (a) 6, (b) 7, (c) 8 and (d) 9 doped with different concentrations.

FIG. 14 shows the EQEs of solution-processable OLEDs doped with compounds 6-9 and Table 2 summarizes the key device performance. As expected, devices with OXD electron-transporting groups are much better than those with PBI moieties with the same linkage mode. For instance, with the para-substituted electron-transporting group, the current efficiency and EQE are increased from 24.5 cd A$^{-1}$ and 7.1% for device made with 6 to 35.1 cd A$^{-1}$ and 9.8% for device doped with 8. The discrepancies on device efficiencies are believed to be due to a better electron-transporting property of OXD than PBI. More importantly, the device performances can be further boosted up by the introduction of meta-substitution. Devices with meta-substituted PBI moieties (i. E. 7) are much more superior to those with para-substituted counterpart (i. E. 6), in which both current efficiency and EQE are increased by ~64% via meta-linkage.

Similar EQE increment can be obtained for devices with OXD electron-transporting groups (i. E. 8 and 9). High current efficiency of 57.4 cd A$^{-1}$ and EQE of 16.0% can be realized for devices made with 9. Such high EQE value is one of the highest amongst solution-processable PHOLEDs based on platinum(II) complexes, as well as solution-processable PHOLEDs based on bipolar iridium(III) and gold (III) complexes.

Example 7

The same materials and processing procedures were employed as described in Example 5, except that compounds 12 and 13 were doped into TCTA:MCP (1:3) as light-emitting layer.

Figure 15:
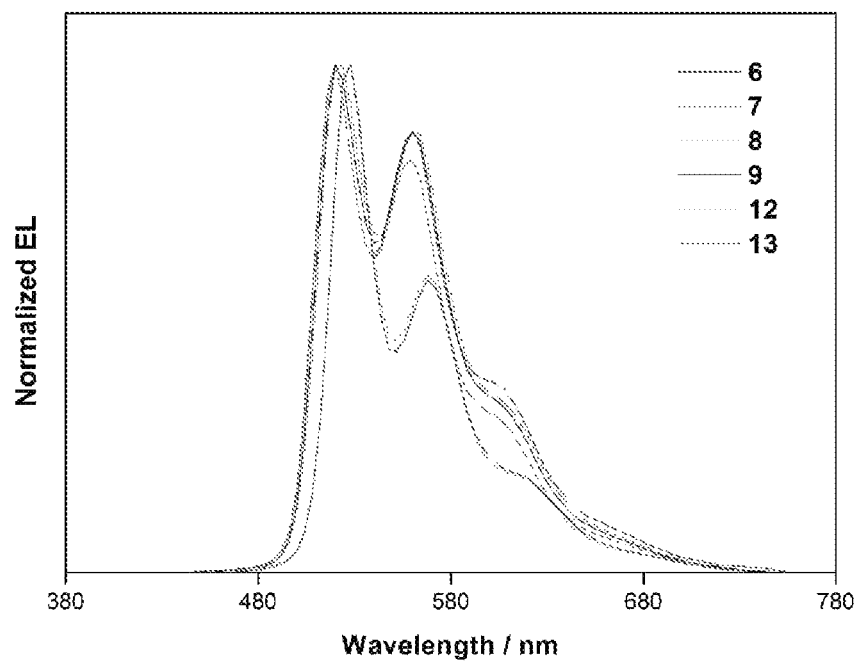
FIG. 15 shows the normalized EL spectra of solution-processable OLEDs doped with 15 wt % 6-9, 12 and 13.

FIG. 15 shows the normalized EL spectra of devices doped with 6-9, 12 and 13 at a current density of 20 mA cm$^{-2}$. In good agreement with the emission studies, the EL spectra of devices made with compounds 12 and 13 have been slightly red shifted by ~8 nm. Such red shift could be rationalized by the direct incorporation of the carbazole dendrimers at the 5-position of the bzimb ligand, leading to the destabilization of the HOMO energy level in 12 and 13.

TABLE 2

Key parameters of solution-processsable OLEDs based on compounds 6-9, 12 and 13

| Complex | Dopant Concentration/ wt % | Max. Current Efficiency/cd A$^{-1}$ | Max. Power Efficiency/lm W$^{-1}$ | Max. EQE/% | CIE (x, y)[a] |
|---|---|---|---|---|---|
| 6 | 15 | 24.5 | 8.1 | 7.1 | 0.38, 0.59 |
| 7 | 10 | 43.6 | 18.3 | 12.1 | 0.36, 0.61 |
| 8 | 10 | 35.1 | 14.7 | 9.8 | 0.37, 0.60 |
| 9 | 15 | 57.4 | 27.7 | 16.0 | 0.37, 0.60 |
| 12 | 15 | 19.2 | 12.5 | 5.3 | 0.37, 0.60 |
| 13 | 20 | 17.7 | 10.1 | 5.0 | 0.38, 0.60 |

[a]Data were collected at a current density of 20 mA cm$^{-2}$.

The invention claimed is:

1. A luminescent dendrimer comprising a cyclometalated tridentate platinum (II) compound comprising one monoanionic auxiliary ligand and a tridentate ligand coordinated to a platinum (II) metal center and having the chemical structure represented by the following general formula (I),

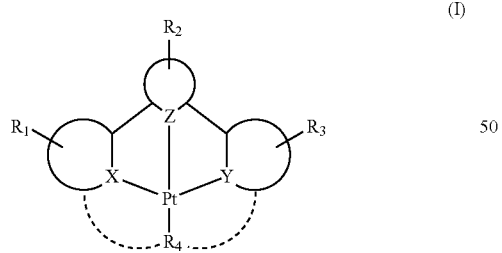

(I)

wherein
   (a) X, Y and Z are cyclic structures;
   (b) any combinations of the rings X, Y and Z can be fused together with each other or the rings X, Y and Z can be non-fused with each other;
   (c) R$_1$, R$_2$ and R$_3$ are the same or different and independently selected from hydrogen, alkyl, alkenyl, alkynyl, alkylaryl, cycloalkyl, OR, NR$_2$, SR, C(O)R, C(O)OR, C(O)NR$_2$, CN, CF$_3$, NO$_2$, SO$_2$, SOR, SO$_3$R, halo, aryl, heteroaryl, heterocyclic group or a dendrimeric moiety of general formula (II), wherein R is independently alkyl, alkenyl, alkynyl, alkylaryl, aryl or cycloalkyl, with at least one of R$_1$, R$_2$, and R$_3$ being a dendrimeric moiety of general formula (II), each being optionally substituted;

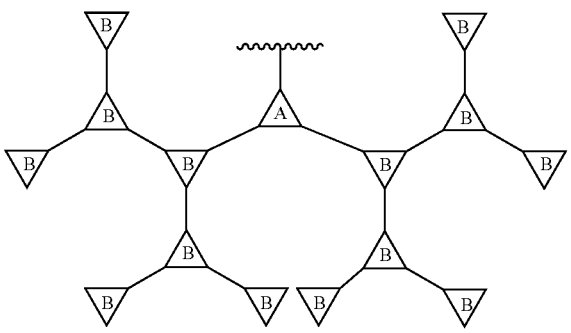

(II)

wherein:
   (i) Unit A in general formula (II) is the central part of the dendron and the branching point of the dendrimer; and
   (ii) Unit B in general formula (II) is the surface groups or dendron of the dendrimer, or none; and
(d) R$_4$ is selected from the following:

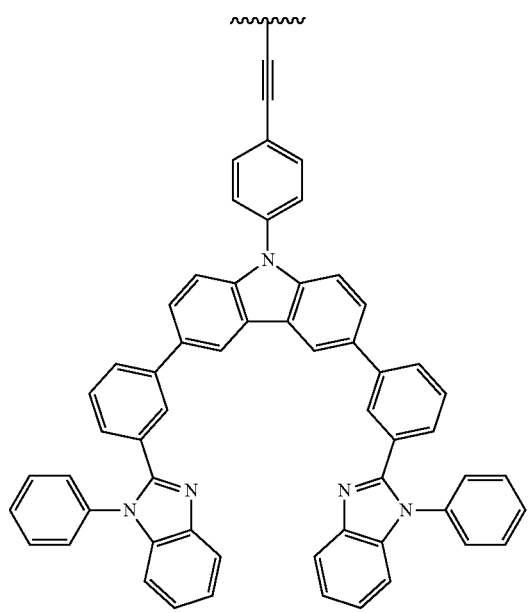

Ligand L3

Ligand L4

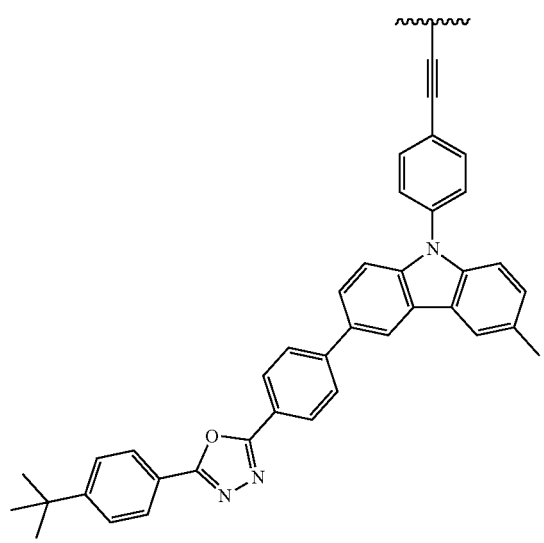

Ligand L6

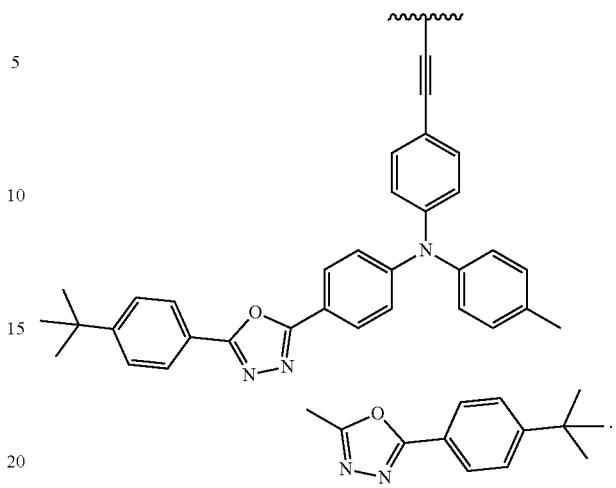

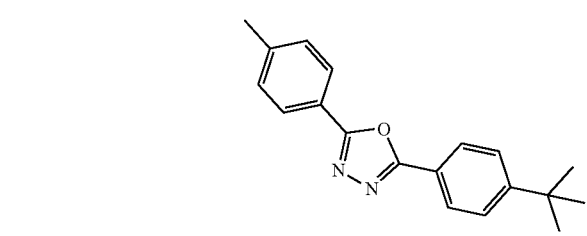

Ligand L5

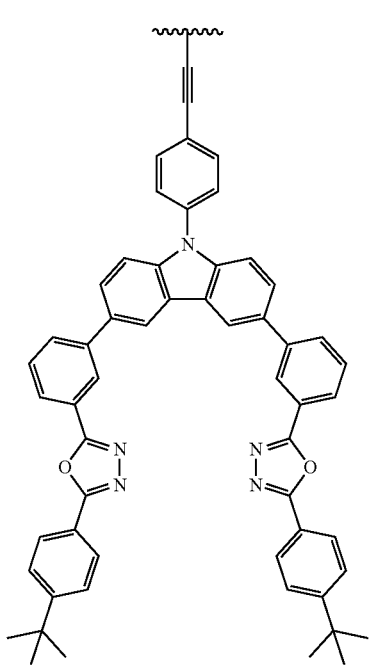

2. The luminescent dendrimer according to claim 1, wherein the X and Y are independently selected from pyridine, imidazole, benzimidazole, naphthoimidazole, quinoline, isoquinoline, quinoxaline, pyrimidine, pyrazine, pyrazole, triazole, tetrazole, pyridazine, triazine, tetrazine, triazole, indole, oxazole, isoxazole, isothiazole, benzothiazole and benzoxazole, each being optionally substituted.

3. The luminescent dendrimer according to claim 1, wherein the Z is selected from benzene, naphthalene, anthracene, pyrene, fluorene, pyrene, pyridine, imidazole, benzimidazole, naphthoimidazole, quinoline, isoquinoline, quinoxaline, pyrimidine, pyrazine, pyrazole, triazole, tetrazole, pyridazine, triazine, tetrazine, triazole, indole, oxazole, isoxazole, isothiazole, benzothiazole, benzoxazole, thiophene, furan, benzofuran and dibenzofuran, each being optionally substituted.

4. The luminescent dendrimer according to claim 1, wherein Unit A and Unit B are optionally substituted N atom, C atom, benzene, phenyl derivatives, pyridine or pyridyl derivatives, thiophene, furan, pyrazole, imidazole, oxazole, isoxazole, thiazole, isothiazole, pyrrole, pyrazine, pyridazine, pyrimidine, benzimidazole, benzofuran, benzothiazole, indole, naphthalene, triazole, tetrazole, pyran, thiapyran, oxadiazole, triazine, tetrazine, carbazole, dibenzothiophene, or dibenzofuran.

5. The luminescent dendrimer according to claim 1, wherein the compound is deposited as a layer on a substrate layer.

6. The luminescent dendrimer according to claim 5, wherein the layer is deposited by vacuum deposition technique.

7. The luminescent dendrimer according to claim 5, wherein the layer is deposited by spin-coating or inkjet printing.

8. The luminescent dendrimer according to claim 1, wherein the compound has photoluminescence properties within a range of about 380 to 1050 nm.

9. The luminescent dendrimer according to claim 1, wherein the compound emits light in response to the passage of an electric current or to an electric field.

10. A light-emitting device with an ordered structure comprising an anode, a hole-transporting layer, a light-emitting layer, an electron-transporting layer and a cathode, wherein the light-emitting layer comprises a platinum (II)

compound having a chemical structure represented by the following general formula (I),

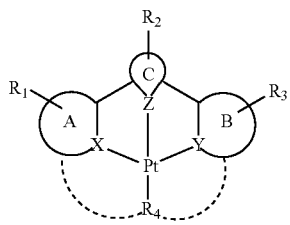

wherein X and Y are independently selected from pyridine, imidazole, benzimidazole, naphthoimidazole, quinoline, isoquinoline, quinoxaline, pyrimidine, pyrazine, pyrazole, triazole, tetrazole, pyridazine, triazine, tetrazine, triazole, indole, oxazole, isoxazole, isothiazole, benzothiazole and benzoxazole, each being optionally substituted; Z is selected from benzene, naphthalene, anthracene, pyrene, fluorene, pyrene, pyridine, imidazole, benzimidazole, naphthoimidazole, quinoline, isoquinoline, quinoxaline, pyrimidine, pyrazine, pyrazole, triazole, tetrazole, pyridazine, triazine, tetrazine, triazole, indole, oxazole, isoxazole, isothiazole, benzothiazole, benzoxazole, thiophene, furan, benzofuran and dibenzofuran, each being optionally substituted; $R_1$, $R_2$ and $R_3$ are the same or different and independently selected from hydrogen, alkyl alkenyl, alkynyl, alkylaryl, cycloalkyl, OR, $NR_2$, SR, C(O)R, C(O)OR, C(O)$NR_2$, CN, $CF_3$, $NO_2$, $SO_2$, SOR, $SO_3R$, halo, aryl, heteroaryl, heterocyclic group or a dendrimeric moiety of general formula (II), wherein R is independently alkyl, alkenyl, alkynyl, alkylaryl, aryl, cycloalkyl, or dendrimeric moieties of general formula (II), each being optionally substituted, with at least one of $R_1$, $R_2$, and $R_3$ being a dendrimeric moiety of general formula (II);

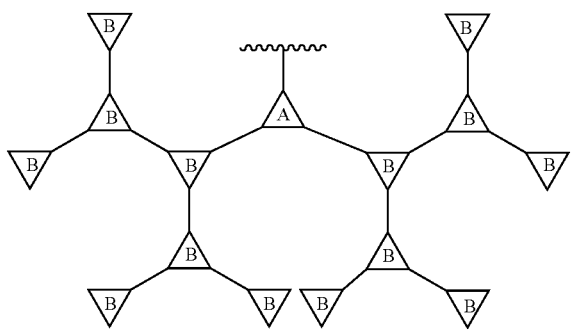

wherein:
(i) Unit A in general formula (II) is the central part of the dendron and the branching point of the dendrimer; and
(ii) Unit B in general formula (II) is the surface groups or dendron of the dendrimer, or none; and wherein $R_4$ is selected from the following:

Ligand L3

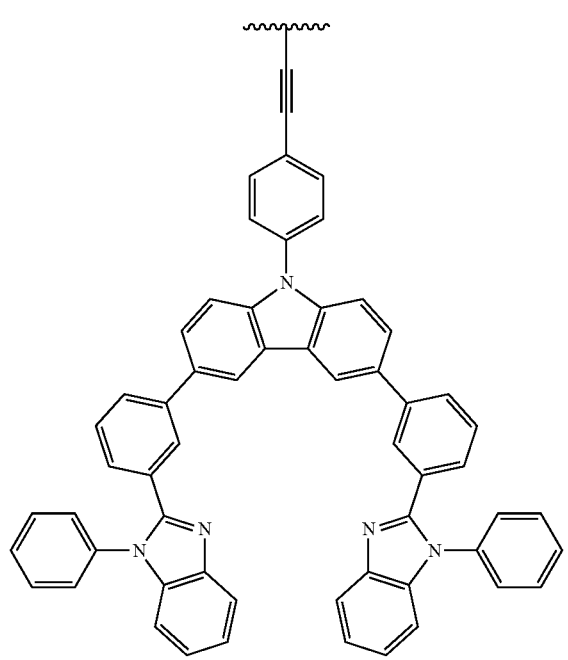

-continued
Ligand L4
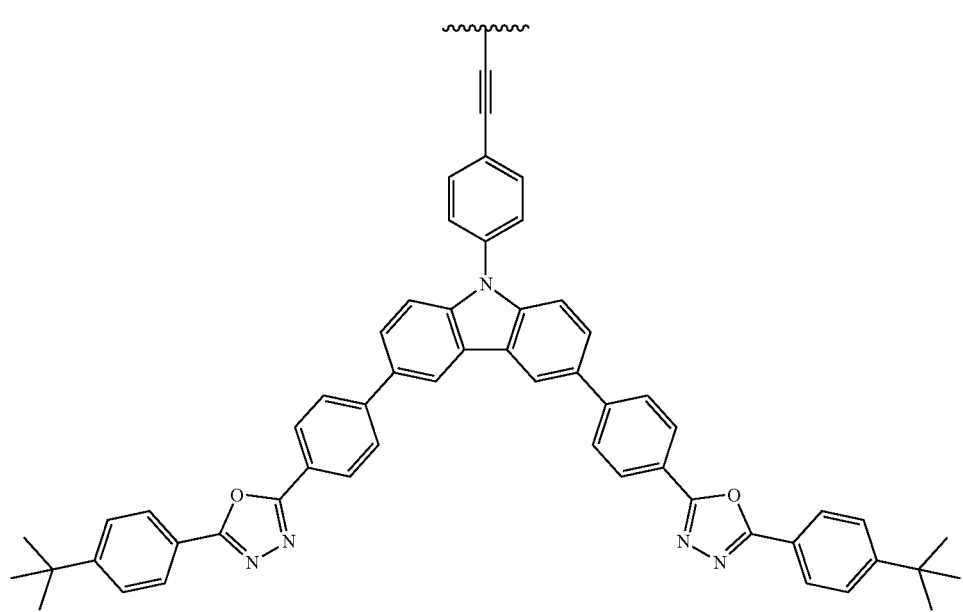
Ligand L5
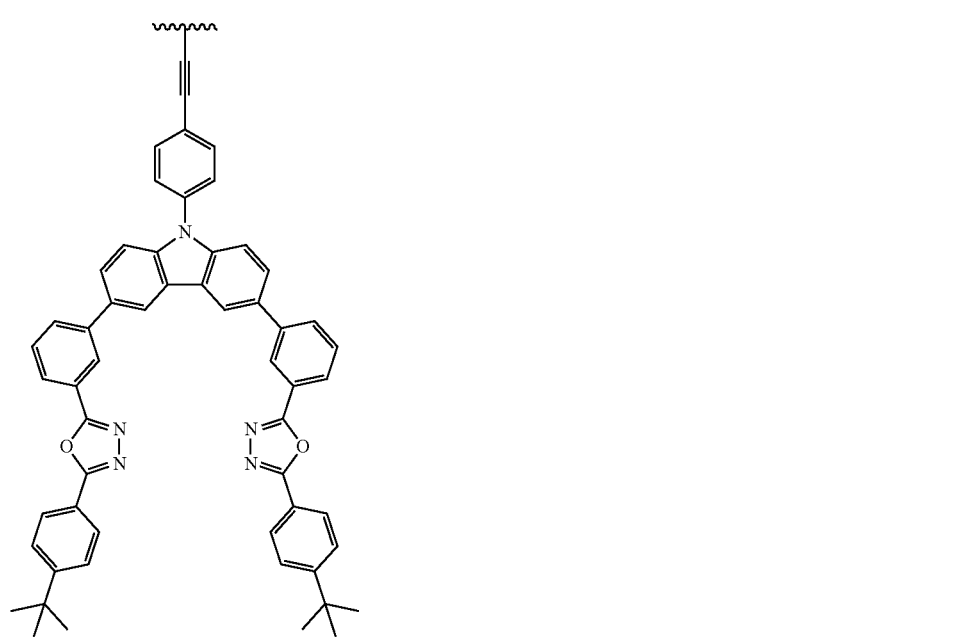
Ligand L6
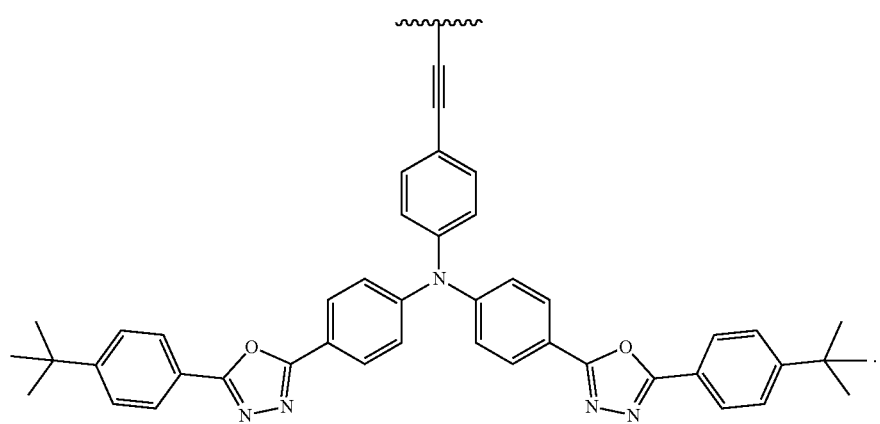

11. The light-emitting device of claim 10, wherein the light-emitting layer is prepared using vacuum deposition technique.

12. The light-emitting device of claim 10, wherein the light-emitting layer is prepared using solution processing technique.

* * * * *